US011655462B2

(12) United States Patent
Lee et al.

(10) Patent No.: US 11,655,462 B2
(45) Date of Patent: May 23, 2023

(54) MUTANT MICROORGANISM INTRODUCED WITH HIGHLY ACTIVE MALATE DEHYDROGENASE FOR PRODUCING SUCCINIC ACID AND METHOD OF PRODUCING SUCCINIC ACID USING THE SAME

(71) Applicant: KOREA ADVANCED INSTITUTE OF SCIENCE AND TECHNOLOGY, Daejeon (KR)

(72) Inventors: Sang Yup Lee, Daejeon (KR); Kyung-Jin Kim, Daejeon (KR); Jung Ho Ahn, Daejeon (KR); Hogyun Seo, Daejeon (KR); Jong An Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 125 days.

(21) Appl. No.: 16/490,515

(22) PCT Filed: May 2, 2019

(86) PCT No.: PCT/KR2019/005247
§ 371 (c)(1),
(2) Date: Aug. 30, 2019

(87) PCT Pub. No.: WO2020/075943
PCT Pub. Date: Apr. 16, 2020

(65) Prior Publication Data
US 2021/0332332 A1 Oct. 28, 2021

(30) Foreign Application Priority Data
Oct. 10, 2018 (KR) ........................ 10-2018-0120696

(51) Int. Cl.
*C12N 1/20* (2006.01)
*C12N 9/04* (2006.01)
*C12N 15/74* (2006.01)
*C12P 7/46* (2006.01)

(52) U.S. Cl.
CPC ............. *C12N 9/0006* (2013.01); *C12N 1/20* (2013.01); *C12N 15/74* (2013.01); *C12P 7/46* (2013.01); *C12Y 101/01037* (2013.01)

(58) Field of Classification Search
None
See application file for complete search history.

(56) References Cited

U.S. PATENT DOCUMENTS

| | | | | |
|---|---|---|---|---|
| 6,995,002 B2* | 2/2006 | Molenaar | ............... | C12P 13/08 435/189 |
| 2010/0068774 A1 | 3/2010 | Fukui et al. | | |
| 2011/0229945 A1 | 9/2011 | Jansen et al. | | |
| 2012/0040422 A1 | 2/2012 | Jansen et al. | | |
| 2013/0217087 A1 | 8/2013 | Lee et al. | | |
| 2013/0302866 A1 | 11/2013 | Finley et al. | | |
| 2014/0363862 A1 | 12/2014 | Rush et al. | | |
| 2015/0057425 A1 | 2/2015 | Van De Graaf et al. | | |

FOREIGN PATENT DOCUMENTS

| | | |
|---|---|---|
| CN | 101023178 A | 8/2007 |
| CN | 102604880 A | 7/2012 |
| CN | 103249832 A | 8/2013 |
| CN | 104854244 A | 8/2015 |
| JP | 2006320208 A | 11/2006 |
| KR | 1020160114184 A | 10/2016 |
| WO | 2008126896 A1 | 10/2008 |
| WO | WO2009024294 A9 | 2/2009 |
| WO | WO2012030130 A2 | 3/2012 |

OTHER PUBLICATIONS

Kim et al. (Metabolic engineering of Mannheimia succiniciproducens for succinic acid production based on elementary mode analysis with clustering, Biotechnology Journal, vol. 12, pp. 1-10, Jan. 2017 (online Dec. 14, 2016).*
Ahn, J.H., et al., "Production of Succinic Acid by Metabolically Engineered Microorganisms", "Current Opinion in Biotechnology", 2016, pp. 54-66, vol. 42.
Alonso-Gutierrez, J., et al., "Towards Industrial Production of Isoprenoids in *Escherichia coli*: Lessons Learned From CRISPR-Cas9 Based Optimization of a Chromosomally Integrated Mevalonate Pathway", "Biotechnology and Bioengineering", 2018, pp. 1000-1013, vol. 115, No. 4.
Bang, J., et al., "Assimilation of Formic Acid and CO2 by Engineered *Escherichia coli* Equipped With Reconstructed One-Carbon Assimilation Pathways", "PNAS", 2018, pp. E9271-E9279, vol. 115, No. 40.

(Continued)

*Primary Examiner* — Richard G Hutson
(74) *Attorney, Agent, or Firm* — Hultquist, PLLC; Steven J. Hultquist

(57) ABSTRACT

Disclosed are a mutant microorganism for producing succinic acid exhibiting improved activity of conversion of oxaloacetate to malate through the introduction of genes encoding a malate dehydrogenase, wherein an amino acid residue that interacts with a pyrophosphate moiety of NADH through an amide functional group of a main chain of malate dehydrogenase is glutamine (Gln), and a method of producing succinic acid using the same. The mutant microorganism producing succinic acid according to the present invention is capable of producing a high concentration of succinic acid at the highest productivity compared to other mutant microorganisms reported to date when the microorganism is cultured in a limited medium. In addition, the mutant microorganism is capable of producing succinic acid at higher productivity and product concentration through further advanced fermentation technology.

4 Claims, 10 Drawing Sheets
(2 of 10 Drawing Sheet(s) Filed in Color)
Specification includes a Sequence Listing.

(56) References Cited

OTHER PUBLICATIONS

Chen, X., et al., "Effects of Culture Redox Potential on Succinic Acid Production by Corynebacterium Crenatum Under Anaerobic Conditions", "Process Biotechnology", 2012, pp. 1250-1255, vol. 47.
Chen, C., et al., "Substrate Inhibition of the Betaine Aldehyde Dehydrogenase BetB from *Staphylococcus aureus*: Structure-Based Mutational Studies", "Appl. Environ. Microbiol.", 2014, pp. 3992-4002, vol. 80.
Cho, J.S., et al., "CRISPR/Cas9-Coupled Recombineering for Metabolic Engineering of Corynebacterium Glutamicum", "Metab. Eng", 2017, pp. 1-39.
Choi, S., et al., "Highly Selective Production of Succinic Acid by Metabolically Engineered Mannheimia Succiniciproducens and Its Efficient Purification", "Biotechnology and Bioengineering", 2016, pp. 2168-2177, vol. 113, No. 10.
De Arriaga, D., et al., "The Nature of the Substrate Inhibition of Cytoplasmic Malate Dehydrogenase from Phycomyces Blakesleeanus", "Biochimia et Biophysica Acta", 1984, pp. 158-163, vol. 784.
Gibson, D., et al., "Enzymatic Assembly of DNA Molecules up to Several Hundred Kilobases", "Nature Methods", May 2009, pp. 343-347, vol. 6, No. 5.
Hall, M.D., et al., "Crystal Structure of a Ternary Complex of *Escherichia coli* Malate Dehydrogenase Citrate and NAD at 1-9 A Resolution", "J. Mol. Biol.", 1993, pp. 213-222, vol. 232.
Hong, S., et al., "The genome sequence of the capnophilic rumen bacterium Mannheimia succiniciproducens", "Nature Biotechnology", Oct. 2004, pp. 1275-1281, vol. 22, No. 10.
Jang, Y., et al., "Construction and Characterization of Shuttle Vectors for Succinic Acid-Producing Rumen Bacteria", "Applied and Environmental Microbiology", Sep. 2007, pp. 5411-5420, vol. 73, No. 17.

Kuhnert, P., et al., "*Basfia succiniciproducens* gen. nov., sp. nov., a new member of the family Pasteurellaceae solated from bovine rumen", "International Journal of Systematic and Evolutionary Microbiology", 2010, pp. 44-50, vol. 60.
Liang, L., et al., "Increased Production of Succinic Acid in *Escherichia coli* by Overexpression of Malate Dehydrogenase", "Biotechnol. Lett. ", 2011, pp. 2439-2444, vol. 33.
Litsanov, B., et al., "Toward Homosuccinate Fermentation: Metabolic Engineering of Corynebacterium Glutamicum for Anaerobic Production of Succinate from Glucose and Formate", "Applied and Environmental Microbiology", 2012, pp. 3325-3337, vol. 78, No. 9.
Raval, D., et al., "Malic Dehydrogenase. V. Kinetic Studies of Substrate Inhibition by Oxalacetate", "Biochemistry", Jul. 9, 1962, pp. 220-224.
Vemuri, G.N., et al., "Succinate production in dual-phase *Escherichia coli* fermentations depends on the time of transition from aerobic to . . . ", "J. Ind. Microbiol. Biotechnol.", Jun. 2002, pp. 325-332, vol. 28, No. 6.
Wang, W., et al., "Production of Succinate by a pflB ldhA Double Mutant of *Escherichia coli* Overexpressing Malate Dehydrogenase", "Bioprocess Biosystem Eng", 2009, pp. 737-745, vol. 32.
NCBI, "malate dehydrogenase [Corynebacterium glutamicum]", NCBI Reference Sequence Database, May 15, 2013.
English Translation of Office Action cited in counterpart Chinese Patent Application No. 201980002422.3 on Feb. 27, 2023.
Search Report issued in counterpart Chinese Patent Application No. 201980002422.3 dated Feb. 16, 2023.
Office Action cited in counterpart Chinese Patent Application No. 201980002422.3 dated Feb. 27, 2023.
Liang, L., et al., "Effect of overexpression of malate dehydrogenase on succinic acid production in *Escherichia coli* NZN111", Chin J. Biotech, 2011, pp. 1005-1012, vol. 27, No. 7.

* cited by examiner

MUTANT MICROORGANISM INTRODUCED WITH HIGHLY ACTIVE MALATE DEHYDROGENASE FOR PRODUCING SUCCINIC ACID AND METHOD OF PRODUCING SUCCINIC ACID USING THE SAME

CROSS-REFERENCE TO RELATED APPLICATIONS

This application is a U.S. national phase under the provisions of 35 U.S.C. § 371 of International Patent Application No. PCT/KR19/05247 filed May 2, 2019, which in turn claims the priority under 35 U.S.C. § 119 of Korean Patent Application No. 10-2018-0120696 filed Oct. 10, 2018. The disclosures of International Patent Application No. PCT/KR19/05247 and Korean Patent Application No. 10-2018-0120696 are hereby incorporated herein by reference in their respective entireties, for all purposes.

TECHNICAL FIELD

The present invention relates to a mutant microorganism introduced with a highly active malate dehydrogenase for producing succinic acid and a method of producing succinic acid using the same. More particularly, the present invention relates to a mutant microorganism exhibiting improved activity of conversion of oxaloacetate to malate through the introduction of a gene encoding malate dehydrogenase wherein an amino acid residue included in the main chain of malate dehydrogenase that interacts with a pyrophosphate moiety of NADH through an amide functional group is glutamine (Gln), and a method of producing succinic acid using the same.

BACKGROUND ART

As environmental problems have recently arisen, many attempts have been made to replace the production of useful compounds based on conventional fossil fuels. Accordingly, research has been conducted worldwide to produce bio-based succinic acid from renewable biomass. Succinic acid is a dicarboxylic acid having four carbon atoms and is a useful compound that can be used as a precursor of compounds having high industrial value, such as 1,4-butanediol, γ-butyrolactone, diethyl succinate, N-methyl-2-pyrrolidone and tetrahydrofuran, as well as used as a monomer for various polymers. The importance of succinic acid has been emphasized and a great deal of research is underway on a variety of methods for producing succinic acid as a bio-based material using various microorganisms such as *Actinobacillus succinogenes, Anaerobiospirillum succiniciproducens, Escherichia coli, Mannheimia succiniciproducens, Saccharomyces cerevisiae,* and *Yarrowia lipolytica.*

Modifications of succinic acid-producing strains have been carried out by changing the metabolic pathway of succinic acid-producing strains. The strategy is to strengthen carbon metabolism and eliminate or reduce the formation of byproducts to thereby improve the metabolic pathway to succinic acid. That is, succinic acid production can be increased by introducing or strengthening genes involved in metabolic pathways of succinic acid, or deleting or weakening genes that inhibit metabolic pathways of succinic acid. As a gene involved in metabolic pathways of succinic acid, malate dehydrogenase is an enzyme introduced in order to increase the production of succinic acid and research relating thereto has been made with the goal of improving the production of succinic acid through introduction thereof. For example, malate dehydrogenase (MDH) facilitates the conversion of oxaloacetate into malate, and this enzyme plays a key role in focusing the metabolic flux toward succinic acid production and there have been made attempts to increase the production of succinic acid by introducing, into microorganisms, *Arabidopsis thaliana*-derived MDH (Kim et al., Biotechnology journal, 12(2), 1600701), *S. cerevisiae*-derived MDH (US 2011-0229945 A1, US 2012-0040422 A1, US 2015-0057425 A1, US 2013-0302866 A1), *Rhizopus delemar*-derived MDH (US 2014-0363862 A1), and *E. coli*-derived MDH (Wang et al., Bioprocess. Biosyst. Eng. 2009, 32:737-745, Liang et al., Biotechnology letters, 33(12), 2439-2444). However, even though the microorganism-derived MDH is introduced, the productivity of succinic acid is low. For this reason, there have been attempts to further metabolically engineer the succinic acid producing strain or optimize the fermentation process to enhance succinic acid production (Ahn et al., Curr. Opin. Biotechnol. 42: 54-66), but there remains a need for additional improvement.

Therefore, the present inventors searched for a method of significantly improving the productivity of succinic acid as compared to conventional methods, and conducted structural analysis of major enzymes of rumen bacteria including *M. succiniciproducens* and other succinic acid-producing microorganisms, based on the fact that extended research has not yet been made on the kinetics or structure of the major enzymes involved in the production of succinic acid. As a result, the present inventors first discovered the structures of *Corynebacterium glutamicum* and *M. succiniciproducens* MDHs in order to develop highly productive succinic acid-producing strains through introduction of MDHs with reduced substrate inhibition and found that it was possible to develop succinic acid-producing strains with maximized productivity. Based on this finding, the present invention has been completed.

DISCLOSURE

Technical Problem

Therefore, it is an object of the present invention to provide a mutant microorganism exhibiting enhanced productivity of succinic acid and a method for maximizing productivity of succinic acid using the same.

Technical Solution

In accordance with the present invention, the above and other objects can be accomplished by the provision of a mutant microorganism obtained by introducing a gene encoding a malate dehydrogenase into a microorganism having the ability to produce succinic acid, wherein the malate dehydrogenase includes glutamine (Gln) as an amino acid residue that interacts with a pyrophosphate moiety of NADH through an amide functional group.

In accordance with another aspect of the present invention, provided is a method for producing succinic acid including: (a) culturing the mutant microorganism to produce succinic acid and (b) recovering the produced succinic acid.

DESCRIPTION OF DRAWINGS

The patent or application file contains at least one drawing executed in color. Copies of this patent or patent application publication with color drawing(s) will be provided by the Office upon request and payment of the necessary fee.

The above and other objects, features and other advantages of the present invention will be more clearly understood from the following detailed description taken in conjunction with the accompanying drawings, in which.

BEST MODE

Unless defined otherwise, all technical and scientific terms used herein have the same meanings as appreciated by those skilled in the field to which the present invention pertains. In general, the nomenclature used herein is well-known in the art and is ordinarily used.

Figure 1:
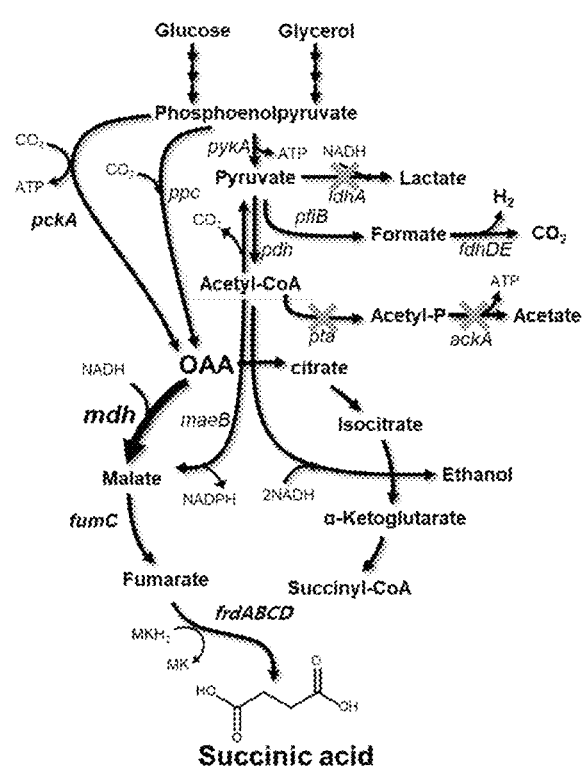
FIG. 1 is a schematic diagram showing a metabolic pathway to succinic acid.
Figure 2:
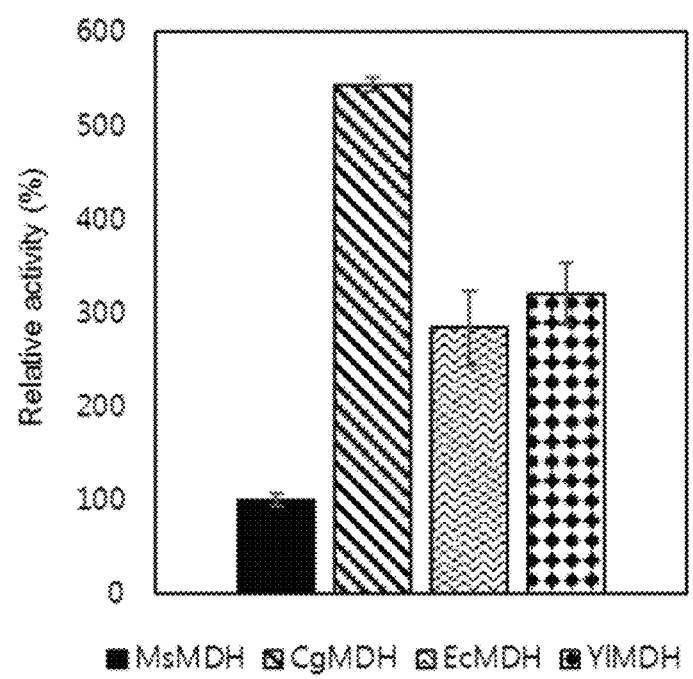
FIG. 2 shows the relative activity of the NADH conversion rate of each MDH.

In the present invention, MDH was selected among candidate enzymes for enhancing a metabolic pathway to succinic acid and consequently overproducing succinic acid. MDH is encoded by the mdh gene, which is an enzyme utilizing oxaloacetate as a substrate (FIG. 1). In order to investigate the effects of MDHs from various strains to produce succinic acid and to find the MDH that most effectively converts oxaloacetate, which is a substrate of MDH, eight types of MDHs, that are, MDH of *M. succiniciproducens* strains (MsMDH), MDH of *C. glutamicum* strains (CgMDH), MDH of *E. coli* strains (EcMDH), MDH of *A. succinogenes* strains (AsMDH), respective MDHs of the cytoplasm, mitochondria and peroxisome of *S. cerevisiae* strains (ScMDHc, ScMDHm, and ScMDHp) and MDH of *Y. lipolytica* strains (YlMDH) were selected, and among them, only MsMDH, CgMDH, EcMDH and YlMDH were successfully expressed and purified in *E coli*. The activity was compared between the four MDHs using 100 μM of oxaloacetate and 100 μM of NADH as a substrate and cofactor, respectively. The result showed that CgMDH had the highest oxaloacetate reduction rate (FIG. 2). This activity corresponded to 5 times that of MsMDH, followed by YlMDH and EcMDH in order of activity, and they also had 2 times or more than that of MsMDH (FIG. 2). Interestingly, although MsMDH is an MDH of *M. succiniciproducens*, which naturally produces succinic acid, CgMDH and EcMDH, derived from *C. glutamicum* and *E. coli*, which are not bacteria naturally producing succinic acid, had better activity. This result suggests the possibility of producing succinic acid more effectively when CgMDH or EcMDH, rather than MsMDH, is introduced into *M. succiniciproducens*.

Figure 3:
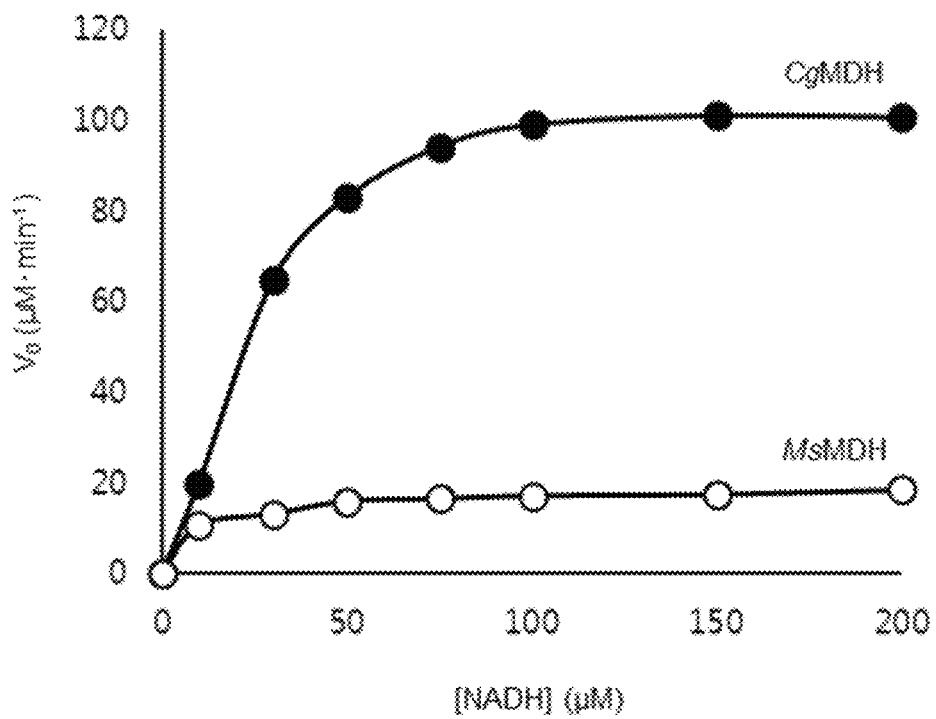
FIG. 3 is a graph showing the NADH conversion rates of CgMDH and MsMDH depending on NADH substrate concentration.
Figure 4:
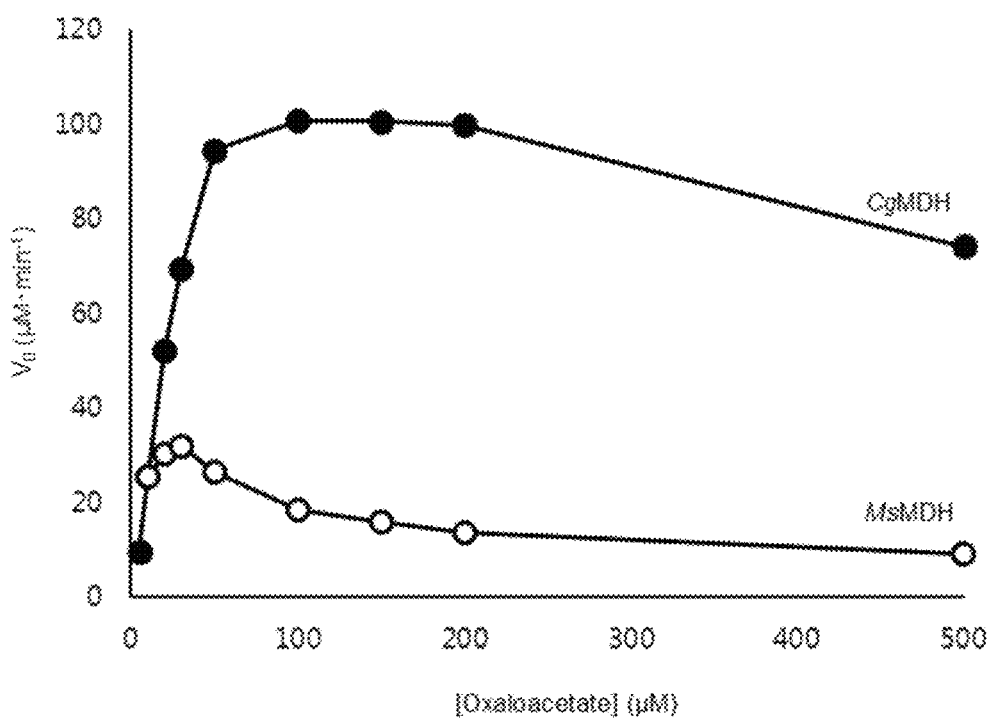
FIG. 4 is a graph showing the NADH conversion rates of CgMDH and MsMDH depending on oxaloacetate substrate concentration.

In order to investigate the results regarding the activity of these enzymes in more detail, kinetic analysis was carried out on the two MDHs having the highest and lowest activity. A graph of an initial velocity with regard to NADH concentration is plotted, based on the Michaelis-Menten model, which indicates again that CgMDH is superior to MsMDH (FIG. 3). However, the graph of MDH reaction rate depending on oxaloacetate concentration showed that both MDHs, particularly MsMDH, was generally inhibited depending on oxaloacetate, the substrate, rather than being saturated (FIG. 4). This substrate inhibition phenomenon was first reported for several dehydrogenases half a century ago (Raval et al., Biochemistry, 2 (2): 220-224, 1963). The mechanism of substrate inhibition suggested in various dehydrogenases may include allosteric regulation, the formation of covalent bonds, the production of non-productive/adsorption complexes with enzymes and the like (Chen et al., Appl. Environ. Microb., 80: 3992-4002, 2014). For example, it is known that NAD$^+$/NADH-dependent MDHs derived from the pig heart form an inactive complex with enol-type oxaloacetate or cytoplasmic MDH derived from *Phycomyces blakesleeanus* inhibits the binding of NADH to the enzyme, thus eventually resulting in the malfunction of the enzyme (De Arriaga et al., Biochim. Biophys. Acta., 784: 158-163, 1984). Inhibition of the enzymatic activity of MsMDH was shown to start from a relatively low oxaloacetate concentration of 30 μM (FIG. 4), and this substrate inhibition action was found to be higher than those of other MDHs (FIG. 4). In summary, these results indicate that MsMDH is disadvantageous in producing succinic acid and CgMDH is the most suitable enzyme for the production of succinic acid among these three MDHs.

Figure 5:
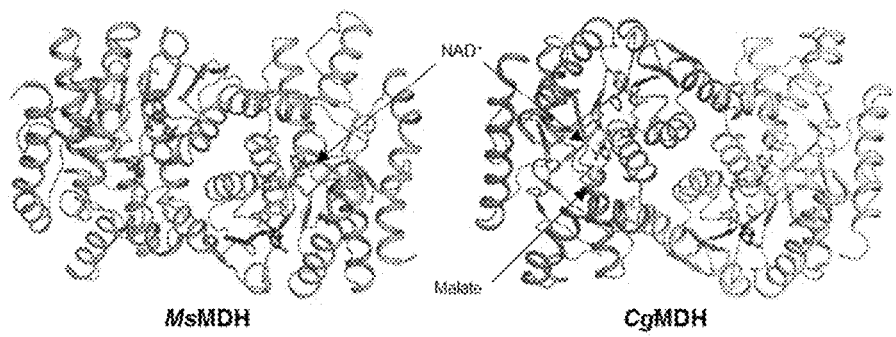
FIG. 5 shows substrate-bound crystal structures of CgMDH and MsMDH, wherein substrates and polypeptide chains are shown in different colors.
Figure 6:
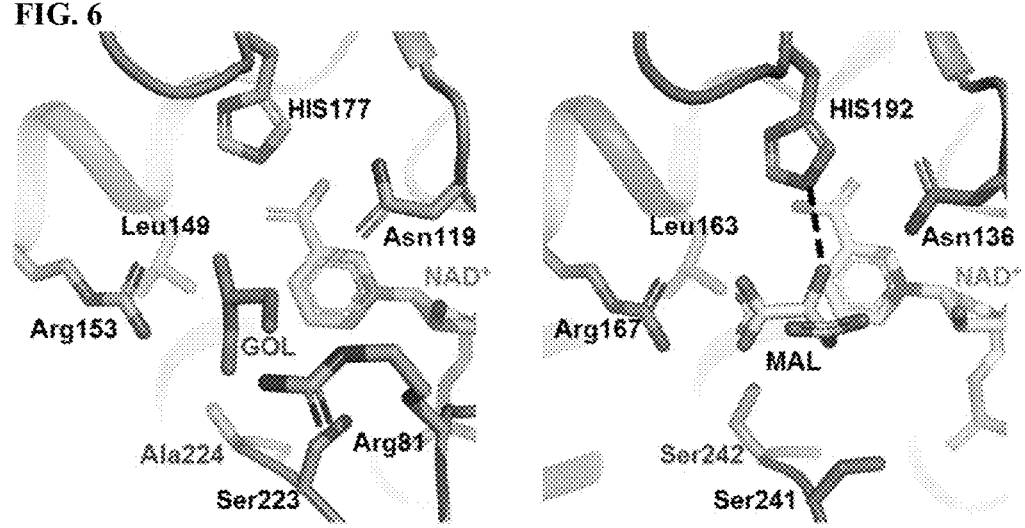
FIG. 6 shows a comparison of amino acid residues near active sites in the structures of CgMDH and MsMDH, wherein the left structure shows MsMDH, the right structure shows CgMDH, GOL represents glycerol, and MAL represents a malate ion.
Figure 7:
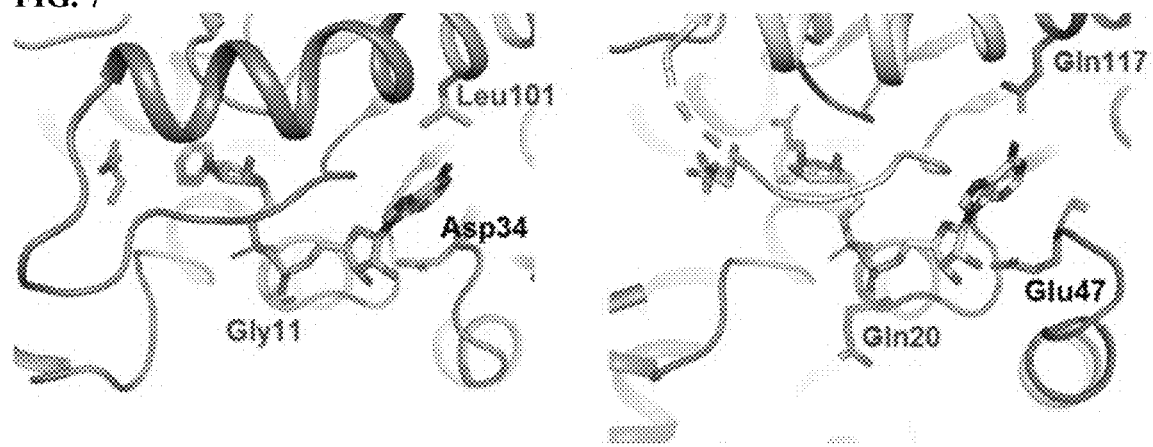
FIG. 7 shows a comparison of amino acid residues near the NAD$^+$/NADH binding sites in the structures of CgMDH and MsMDH, wherein the cover structures conserved in many MDHs are expressed in different colors.

In order to find why CgMDH has better enzyme activity than MsMDH at the molecular level, the crystal structures of the two enzymes were identified and the structure of complex with substrate were also identified (FIG. 5). Both CgMDH and MsMDH form homodimers and belong to the $NAD^+$/NADH-dependent malate and lactate dehydrogenase superfamily (FIG. 5). The N-terminus of CgMDH and MsMDH exhibits a Rossmann fold, consisting of six strands of β-sheets aligned side by side along the α-helices, while the C-terminus forms an α+β fold (FIG. 5). The active sites of the two enzymes are present between specific folds at each terminus, and the $NAD^+$/NADH binding site is particularly related to the Rossmann fold. However, the result of comparison in the structures between the two enzymes showed that there was a great difference of about 2.772 in the value of R.M.S.D. of Cα-backbone. Based on such structural comparison, the present inventors found structural differences that could affect the activity of the enzymes, especially around the active sites (FIGS. 6 and 7). This difference may represent a large difference between the cytosolic MDH and the mitochondrial MDH. The length of the main chains of the rings near the active site, in addition to the corresponding amino acid residues, is different, but the present inventors focused on some different main amino acid residues. For example, amino acid residues corresponding to Ala224, Leu101 and Gly11 located near substrate-binding sites of MsMDH correspond to Ser242, Gln117, and Gln20 of CgMDH, respectively (FIGS. 6 and 7). These structural differences are expected to play a key role to create the difference in the kinetic activities of CgMDH and MsMDH.

Figure 8:
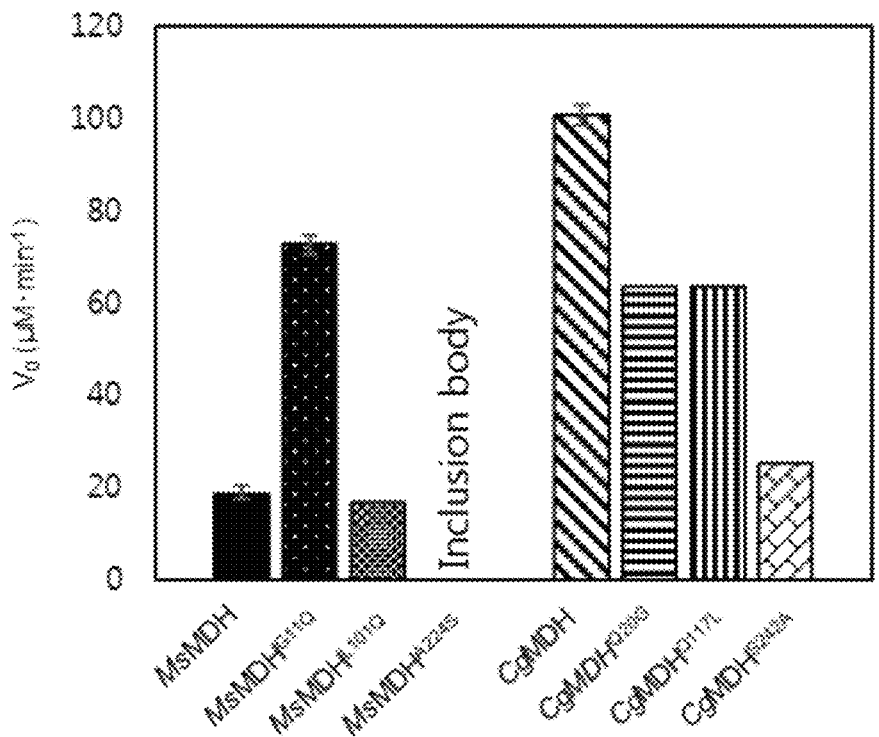
FIG. 8 shows the NADH conversion rates of CgMDH and MsMDH and mutant enzymes thereof.
Figure 9:
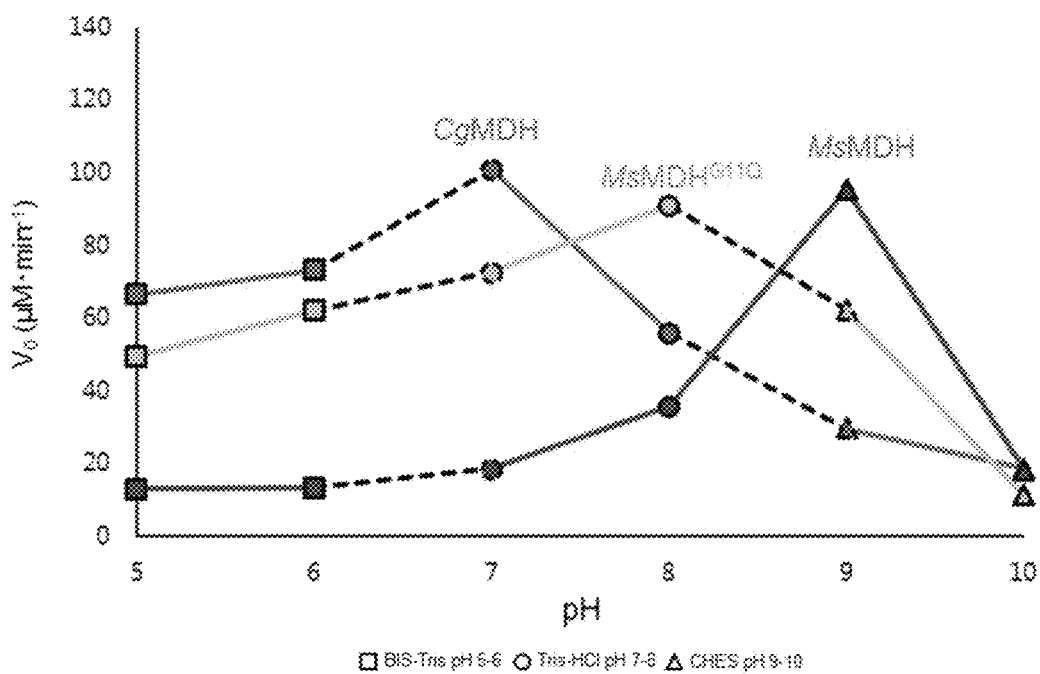
FIG. 9 shows the NADH conversion rates of CgMDH, MsMDH, and MsMDH$^{G11Q}$ mutant enzymes depending on pH in blue, red and yellow, respectively, wherein the conditions using BIS-Tris buffer are shown as squares, the conditions using Tris buffer are shown as circles, and the conditions using glycine buffer are shown as triangles.
Figure 10:
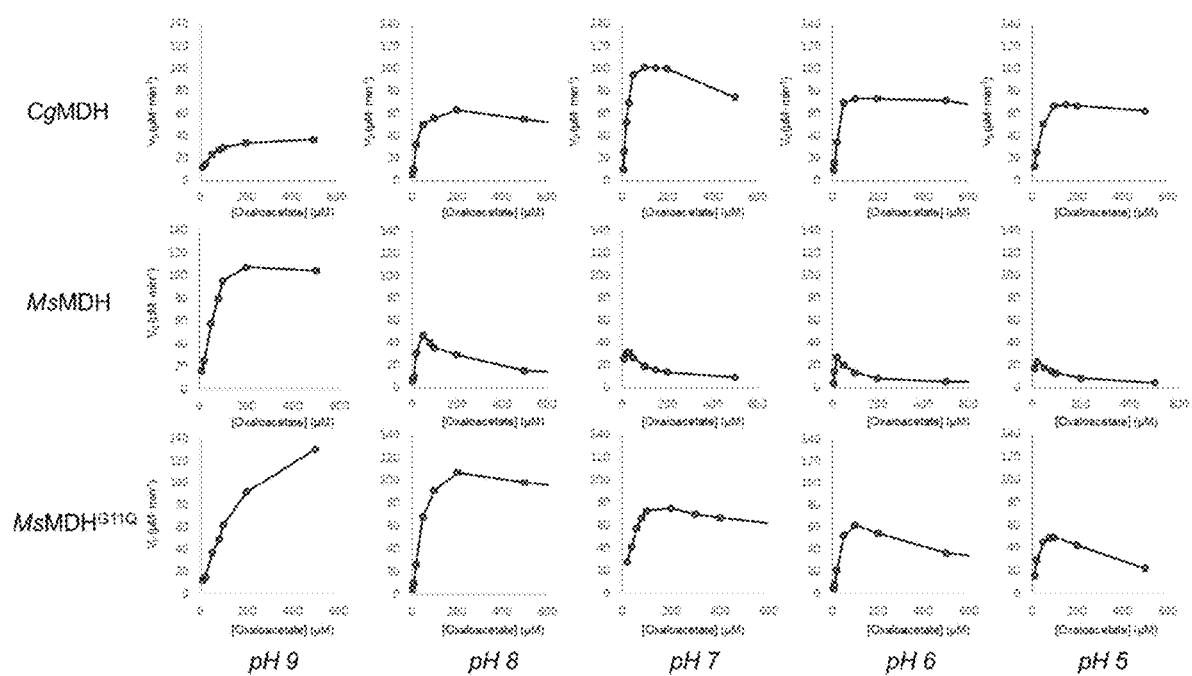
FIG. 10 is a graph showing the NADH conversion rates of CgMDH, MsMDH and MsMDH$^{G11Q}$ depending on oxaloacetate substrate concentrations at pHs of 6.0, 7.0 and 8.0, wherein information about the activity of CgMDH and MsMDH at a pH of 7.0, already provided in FIG. 3, is represented by a dotted line.

In general, it is possible to enhance the enzyme performance by applying the key structural properties of highly active proteins to the target. Therefore, in order to investigate the effect of mutual substitution of key amino acid residues near substrate-binding sites on the activity, different mutant enzymes ($MsMDH^{G11Q}$, $CgMDH^{Q20G}$, $MsMDH^{L101Q}$, $CgMDH^{Q117L}$, $MsMDH^{A224S}$, $CgMDH^{S242A}$) were prepared. These enzymes were expressed in E. coli and all mutant enzymes, excluding $MSMDH^{A224S}$ expressed as inclusion bodies, were successfully purified. All of the mutant enzymes of CgMDH ($CgMDH^{Q20G}$, $CgMDH^{Q117L}$, $CgMDH^{S242A}$) decreased the oxaloacetate conversion rate to less than half of the wild type (FIG. 8). The activity of $MsMDH^{L101Q}$ was also lower than that of MsMDH and the activity of the mutant enzyme, $MsMDH^{G11Q}$, was improved three times than that of MsMDH (FIG. 8). In order to investigate how the substitution of the amino acid at the position 11 is involved in enzymatic activity, three enzymes of CgMDH, MsMDH and $MsMDH^{G11Q}$ were examined. First, the activity thereof was measured depending on pH. As a result, it was found that the optimum pH for CgMDH was about 7.0, and the activity of MsMDH was increased in proportion to alkalinity and the optimum pH therefor was about 9.0 (FIG. 9). The optimal pH for succinic acid production is relatively acidic at about 6.5 (Hong et al., Nat. Biotechnol., 22: 1275-1281, 2004) and this conditional limit demonstrates again the fact that MsMDH is disadvantageous compared to CgMDH in terms of the production of succinic acid. In addition, the optimum pH of $MsMDH^{G11Q}$, having an increase in activity as discovered in the above experiment, was about 8.0, and this optimal pH was found to be lowered by the corresponding mutation (FIG. 9). In order to compare the additional kinetic activity, the reaction rate depending on substrate concentration was determined at each pH (FIG. 10). It was found that, as the pH decreases, the substrate inhibition increases, as is obvious from the results of MsMDH and $MsMDH^{G11Q}$ mutant enzymes as a whole (FIG. 10). As a result, MsMDH was almost free from substrate inhibition at an optimum pH of 9.0 and eventually had the highest activity among these enzymes (FIG. 10). Most notably, however, substrate inhibition of the $MsMDH^{G11Q}$ mutant enzyme was significantly reduced at all pH levels compared to that of MsMDH (FIG. 10). It has been reported that a single mutation of the active site in several dehydrogenases can relieve or eliminate substrate inhibition (Chen et al., Appl. Environ. Microb., 80: 3992-4002, 2014). The substrate inhibition of MDH was reported to affect the binding of NADH and the amino acid residue at the corresponding position 11 was also directly related to the binding of NADH (FIG. 7). Therefore, the pyrophosphate portion of NADH interacting with the position 11 will be interpreted to be closely related to the substrate inhibition. In conclusion, in-vitro studies have shown that CgMDH has an oxaloacetate-reducing activity significantly higher than that of MsMDH at a low pH, and that the introduction of CgMDH, instead of MsMDH, into the succinic acid-producing strain, is predicted to result in a further increase in the production yield of succinic acid. It was found which structural difference caused the difference in the activity through a single amino acid residue mutation. In particular, it was found that the Gly11 residue of MsMDH was involved in serious substrate inhibition activity of the corresponding enzyme protein. It could be predicted that the mutant enzyme $MsMDH^{G11Q}$ would cause the production of succinic acid when introduced into the succinic acid-producing strain, instead of the conventional MsMDH, since the $MsMDH^{G11Q}$ mutant enzyme, in which Gly11 of MsMDH was substituted with Gln, had greater activity than conventional M. succiniciproducens wild-type enzymes. The introduction of the corresponding mutant enzyme can be carried out by substitution of only one amino acid in the conventional enzyme, rather than the introduction of an foreign gene, thus being free from problems such as GMOs.

In fact, to improve the production of succinic acid using MDH exhibiting reduced substrate inhibition, based on in-vitro studies, MDHs showing further reduced substrate inhibition than conventional MDHs were introduced into the M. succiniciproducens PALK (KCTC10973BP) strain. The M. succiniciproducens PALK (KCTC10973BP) strain is a strain obtained by deleting a gene encoding a lactate dehydrogenase, a gene encoding a phosphotransacetylase and a gene encoding an acetate kinase from an M. succiniciproducens wild-type strain, and is a succinic acid-producing mutant microorganism having the property of producing nearly homo-succinic acid at a high concentration in anaerobic condition. In order to identify that the production of succinic acid is improved by introducing MDHs having a reduced effect of substrate inhibition, a M. succiniciproducens PALK (KCTC10973BP) strain that overexpress wild-type MDH was developed before the introducing MDH with better performance. Thus, The developed PALK (pMS3-msmdh) strain produced 79.07 g/L of succinic acid at a yield of 1.23 mol/mol glucose and a productivity of 3.26 g/L/h (FIG. 11; Table 1). Since the MsMDH had the lowest activity in the activity test, the strain overexpressing MsMDH showed little strain improvement effect and only a slight increase in the production of succinic acid. A strain overexpressing CgMDH was developed because, among MDHs, CgMDH showed the highest activity and the lowest substrate inhibition in the in-vitro activity test. The prepared PALK (pMS3-cgmdh) strain produced 87.23 g/L of succinic acid at a yield of 1.29 mol/mol glucose and a productivity of 3.6 g/L/h (FIG. 11; Table 1). The results of fed-batch fermentation of PALK (pMS3), PALK (pMS3-msmdh) and PALK (pMS3-cgmdh) are consistent with the results of identification of the activity of MDH in vitro. In particular, greater improvement in all succinic acid production indicators (production concentration, yield and productivity) by PALK (pMS3-cgmdh) compared to *M. succiniciproducens* PALK (KCTC10973BP) may result from improved conversion of oxaloacetate to malate as well as reduction of a substrate inhibition effect.

The effects of the MDHs (EcMDH derived from *E. coli*, ZrMDH derived from *Zygosaccharomyces rouxii*, and ScMDH2 and ScMDH3 derived from *S. cerevisiae*) reported to be the most effective in improving the production of succinic acid in the literature were also verified in vivo in order to identify whether CgMDH is the best among MDH candidates used to improve production of succinic acid. For this purpose, PALK (pMS3-ecmdh), PALK (pMS3-zrmdh), PALK (pMS3-scmdh2) and PALK (pMS3-scmdh3) overexpressing the respective MDHs were constructed. The results of the fed-batch fermentation of the four constructed MDH-overexpressing strains showed that 79.05, 76.11, 77.34 and 75.15 g/L of succinic acid were produced at productivity of 3.27, 3.15, 3.19 and 3.1 g/L/h and yields of 1.29, 1.25, 1.16 and 1.13 mol/mol glucose, respectively. These results indicate that the succinic acid productivity is improved than that of the PALK (pMS3) strain, not overexpressing MDH, but is lower than that of the PALK (pMS3-cgmdh) strain overexpressing CgMDH. That is, this indicates that, among the MDH candidates, CgMDH has the greatest practical effect on succinic acid production.

PALK (pMS3-cgmdh$^{Q20G}$) and PALK (pMS3-msmdh$^{G11Q}$) strains were constructed in order to confirm, in vivo, the in-vitro observation that the differences in substrate inhibition effects and activity between CgMDH and MsMDH result from the structural differences of the enzymes. The results of fed-batch fermentation of the constructed strain PALK (pMS3-cgmdh$^{Q20G}$) showed that 79.39 g/L succinic acid was produced at a yield of 1.00 mol/mol glucose and productivity of 3.27 g/L/h (FIG. 11; Table 1). The productivity of succinic acid was remarkably decreased compared to the PALK (pMS3-cgmdh) strain, which corroborates the in-vitro result showing that the glutamine at position 20 described above is an important part of the activity of CgMDH.

Figure 11:
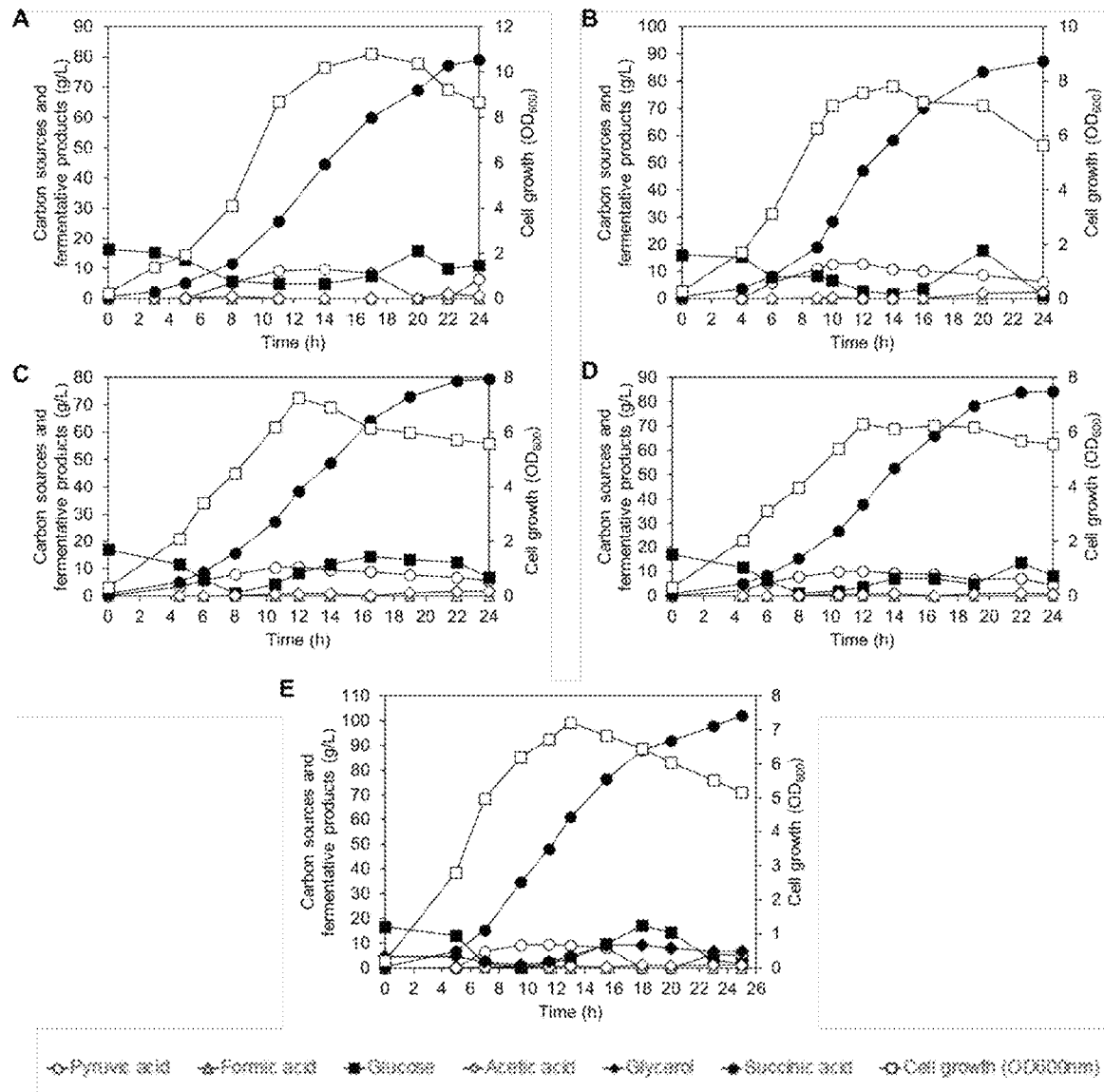
FIG. 11 is a growth and metabolite production curve of *M. succiniciproducens* PALK (pMS3-msmdh) (A), PALK (pMS3-cgmdh) (B), PALK (pMS3-cgmdh$^{Q20G}$) (C) and PALK (pMS3-msmdh$^{G11Q}$) (D) strains through fed-batch culture using glucose as a single carbon source, and is a growth and metabolite production curve of *M. succiniciproducens* PALK (pMS3-cgmdh) (E) through fed-batch culture using a combination of glucose and glycerol as carbon sources.

The results of fed-batch fermentation of the constructed PALK (pMS3-msmdh$^{G11Q}$) strain showed that 84.19 g/L succinic acid was produced at a yield of 1.08 mol/mol glucose and productivity of 3.48 g/L/h (FIG. 11; Table 1). The increased production concentration and productivity of succinic acid compared to the PALK (pMS3-msmdh) strain were found to be similar to the in-vitro results, indicating that changing glycine at position 11 to glutamine results in increased enzymatic activity and reduced substrate inhibition. These in-vivo results show that enzymatic modification based on structural analysis can eventually contribute to the actual improvement of the production of succinic acid.

Particularly, in the present invention, it is known that MDH, which is an enzyme used for the production improvement of succinic acid, plays an important role in the production of succinic acid in *E. coli* and *Corynebacterium* sp. as well as in *Mannheimia* sp., *Basfia* sp., *Actinobacillus* sp. and *Anaerobiospirillum* sp. as rumen bacteria (Lee et al., WO 2012/030130 A2; Liang et al., Biotechnol. Lett., 33(12): 2439-2444, 2011; Chen et al., Process. Biochem., 47:1250-1255, 2012). Therefore, genetic variations in the strains such as those shown in the present invention are commonly applicable for the construction of strains overproducing succinic acid. In particular, *Basfia* sp. was named "*Mannheimia* sp." when it was originally isolated from the bovine rumen along with *Mannheimia* sp., but was classified into "*Basfia* sp." later. *Mannheimia* and *Basfia* strains have substantially similar gene nucleotide sequence sizes of 2,314,078 bp and 2,340,000 bp, and both the strains have the same ratio (i.e., 42.5 mol %) of G and C in the base sequence. In addition, they have 95% homology over the entire genes, and in particular, among 2,380 ORFs of *Mannheimia* and 2,363 ORFs of *Basfia*, 2,006 ORFs are homologous. It should be noted that the homologous 2,006 ORFs are known as core genomes. Also, these strains have considerable identity, for example, 16S rRNA sequence identity of 99.8% and both of them are thus referred to as "*Mannheimia* sp." (Ahn et al., Curr. Opin. Biotech., 42: 54-66, 2016; Scholten et al. al., WO 2009/024294A1; Kuhnert et al., Int. J. Syst. Evol. Microbiol., 60: 44, 2010). That is, in the present invention, *Mannheimia* sp. is intended to include *Basfia* sp., which has been recently found to be substantially the same species.

CgMDH, which actually showed the best effect in the present invention, was introduced into *E. coli* and *C. glutamicum*, which are the most representative industrial succinic acid-producing strains excluding rumen bacteria. As a result, *E. coli* W3110 (p100pro99A-cgmdh) and *C. glutamicum* (pEKEx1-cgmdh) strains each overexpressing CgMDH showed significantly improved productivity of succinic acid than conventional *E. coli* W3110 and wild-type *C. glutamicum* strains not overexpressing CgMDH (Table 2). These results suggest that identical or similar CgMDH overexpression-based engineering can be generally applied to all general bio-based succinic acid-producing strains in order to improve succinic acid production.

Finally, in order to identify that the improvement of succinic acid production by *M. succiniciproducens* PALK (pMS3-cgmdh) and PALK (pMS3-msmdh$^{G11Q}$) strains do not result from the effect of MDH naturally present in *M. succiniciproducens* PALK (KCTC10973BP), the genes encoding MDHs present in the genome of the *M. succiniciproducens* PALK (KCTC10973BP) strain were deleted and genes encoding CgMDH and MsMDH$^{G11Q}$ were inserted therein to construct PALKcgmdh and PALKmsmdh$^{G11Q}$ strains, respectively (Table 1). In addition, it has been known that genes expressed in plasmids may lose their plasmids due to instability of plasmids even if they are retained using antibiotics (Alonso-Gutierrez et al., Biotechnol. Bioeng., 115(4):1000-1013, 2018). In consideration of this, the direct insertion of genes into the genome may be beneficial in constructing more stable strains. This method is generally used due to the advantage of eliminating the necessity to use expensive antibiotics in order to retain the plasmids.

Figure 13:
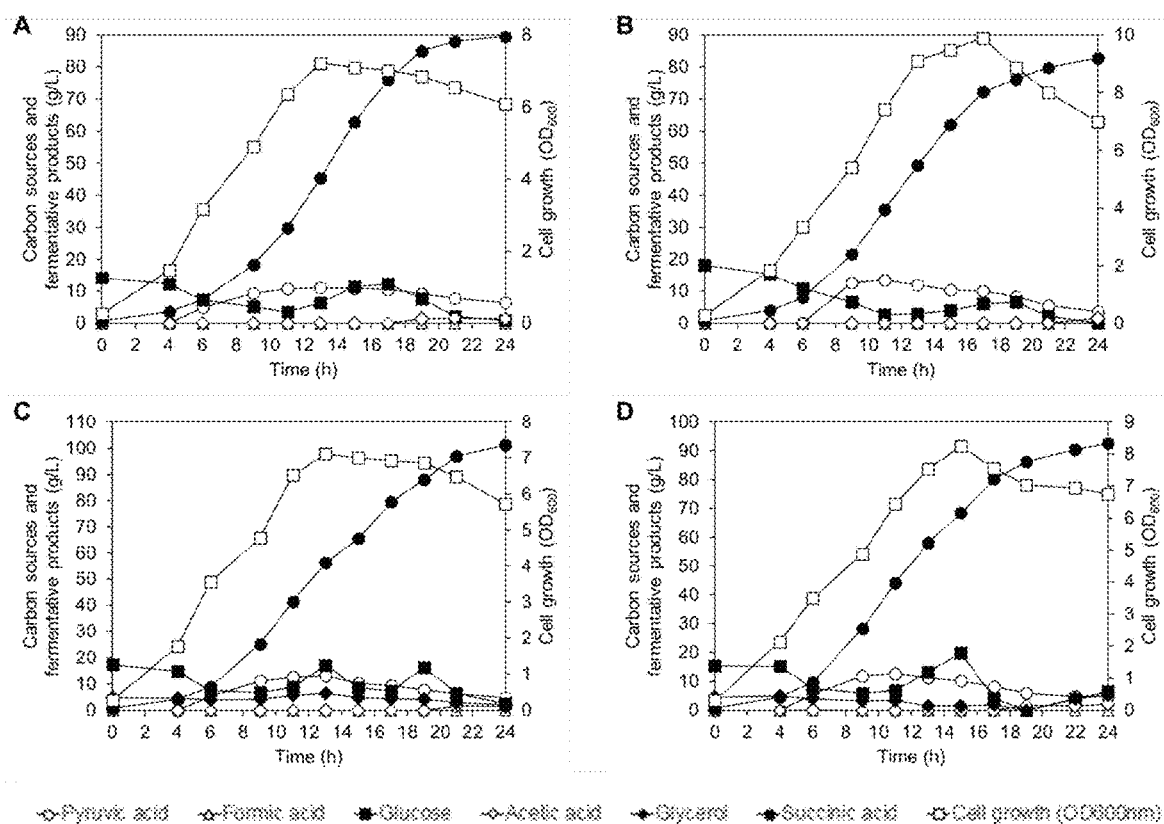
FIG. 13 is a growth and metabolite production curve showing the results of fed-batch culture of an *M. succiniciproducens* PALKcgmdh strain using glucose as a single carbon source (A) and using a combination of glucose with glycerol as carbon sources (C) and of an *M. succiniciproducens* PALKmsmdh$^{G11Q}$ strain using glucose as a single carbon source (B) and using a combination of glucose and glycerol as carbon sources (D)

As a result of fed-batch fermentation, the constructed PALKcgmdh strain produced 89.6 g/L of succinic acid at a yield of 1.28 mol/mol glucose and productivity of 3.71 g/L/h (FIG. 13; Table 1). As a result of fed-batch fermentation, the PALKmsmdh$^{G11Q}$ strain produced 82.76 g/L of succinic acid at a yield of 1.13 mol/mol glucose and productivity of 3.42 g/L/h (FIG. 13; Table 1).

The results of comparison of succinic acid productivity between the PALKcgmdh strain and the PALKmsmdh$^{G11Q}$ strain showed that MDHs naturally present in the *M. succiniciproducens* PALK (KCTC10973BP) strain did not have a great effect on overproduction of succinic acid by PALK (pMS3-cgmdh) and PALK (pMS3-msmdh$^{G11Q}$) strains. Eventually, it was found that the effect of improving succinic acid production of the *M. succiniciproducens* PALK (pMS3-cgmdh) strain and the PALK (pMS3-msmdh$^{G11Q}$) strain also resulted from CgMDH and MsMDH$^{G11Q}$ showing reduced substrate inhibition.

In order to further improve succinic acid production of the constructed PALKcgmdh and PALKmsmdh$^{G11Q}$ strains, fed-batch fermentation was conducted in a chemically defined medium using both glucose and glycerol as dual carbon sources. Glycerol as a secondary carbon source offers twice as much reducing equivalents per mole than utilizing glucose as sole carbon source. In addition, 1 mol of NADH is required to convert oxaloacetate to malate through MDH. Thus, glycerol utilization is helpful for the production of succinic acid (Choi et al., Biotechnol. Bioeng., 113 (10): 2168-2177, 2016). The results of fed-batch fermentation of the PALKcgmdh strain in a limited medium using both glucose and glycerol as dual carbon sources showed that 101.18 g/L of succinic acid was produced at a yield of 1.37 mol/mol glucose and productivity of 4.18 g/L/h (when both glucose and glycerol are used as dual carbon sources, the yield was expressed based on glucose in consideration of the number of carbon atoms of the two carbon sources for easy comparison in yield, and hereinafter referred to as "mol/mol glucose" in this case) (FIG. 13; Table 1). These results are similar to the fed-batch fermentation results of the PALK (pMS3-cgmdh) strain, conducted in the same medium and using the same carbon source (FIG. 11; Table 2). This result shows the highest succinic acid productivity among the results of conducted fermentation without using any additional complicated fermentation methods such as dual-phase fermentation.

The PALKmsmdh$^{G11Q}$ strain was subjected to fed-batch fermentation using both glucose and glycerol as dual carbon sources in the limited medium. As a result, 92.5 g/L of succinic acid was produced in a yield and productivity of 1.28 mol/mol glucose and 3.82 g/L/h, respectively (FIG. 13; Table 1). Although the succinic acid productivity thereof was not superior to that of the PALKcgmdh strain, this result indicates that the productivity of succinic acid of the PALKmsmdh$^{G11Q}$ strain can be improved by reducing the substrate inhibition of MDH, as compared to the *M. succiniciproducens* PALK (KCTC10973BP) strain and corroborates the in-vitro result (Table 1).

Therefore, in one aspect, the present invention is directed to a mutant microorganism obtained by introducing a gene encoding a malate dehydrogenase into a microorganism having the ability to produce succinic acid, wherein, in the malate dehydrogenase, an amino acid residue, which is positioned at the terminus of the first alpha-helix of malate dehydrogenase and interacts with a pyrophosphate moiety of NADH through an amide functional group, is glutamine (Gln).

The term "interaction" means binding of the amide functional group of the main chain of the malate dehydrogenase to the pyrophosphate moiety of NADH through electrical attraction to stabilize the pyrophosphate moiety. In the present invention, the malate dehydrogenase may be i) a malate dehydrogenase derived from *Corynebacterium glutamicum* represented by the amino acid sequence of SEQ ID NO: 40; or ii) a malate dehydrogenase wherein an 11$^{th}$ amino acid of the malate dehydrogenase derived from *Mannheimia succiniciproducens* represented by an amino acid sequence of SEQ ID NO: 42 is substituted with glutamine, but the present invention is not limited thereto.

In the present invention, the gene encoding i) the malate dehydrogenase derived from *Corynebacterium glutamicum* is represented by the nucleotide sequence of SEQ ID NO: 41 and the gene encoding ii) the malate dehydrogenase derived from *Mannheimia succiniciproducens* is represented by the nucleotide sequence of SEQ ID NO: 43, but the present invention is not limited thereto.

That is, although specific amino acid sequences and nucleotide sequences are described in the present invention, it will be apparent to those skilled in the art that amino acid sequences substantially identical to the enzymes to be implemented in the present invention and the nucleotide sequences encoding the same fall within the scope of the present invention. The term "substantially identical" includes the case where the amino acid or nucleotide sequence is highly homologous and the case of a protein that shares the structural characteristics regardless of the homology of the sequence or has the same function as that used in the present invention. The present invention may include an enzyme having a partial deletion of a sequence other than the sequence constituting the core of the present invention or a fragment of a nucleotide sequence encoding the same, and may include all amino-acid or nucleotide sequences having the same function as that used in the present invention regardless of the length of the fragment.

In the present invention, the malate dehydrogenase derived from *Corynebacterium glutamicum* may be represented by the following SEQ ID NO: 40.

SEQ ID NO: 40
MNSPQNVSTKKVTVTGAAGQISYSLLWRIANGEVFGTDTPVELKLLEIPQA

LGGAEGVAMELLDSAFPLLRNITITADANEAFDGANAAFLVGAKPRGKGEE

RADLLANNGKIFGPQGKAINDNAADDIRVLVVGNPANTNALIASAAAPDVP

ASRFNAMMRLDHNRAISQLATKLGRGSAEFNNIVVWGNHSATQFPDITYAT

VGGEKVTDLVDHDWYVEEFIPRVANRGAEIIEVRGKSSAASAASSAIDHMR

DWVQGTEAWSSAAIPSTGAYGIPEGIFVGLPTVSRNGEWEIVEGLEISDFQ

RARIDANAQELQAEREAVRDLL

In the present invention, the gene encoding the malate dehydrogenase derived from *Corynebacterium glutamicum* may be represented by the following SEQ ID NO: 41.

SEQ ID NO: 41
ATGAATTCCCCGCAGAACGTCTCCACCAAGAAGGTCACCGTCACCGGCGCA

GCTGGTCAAATCTCTTATTCACTGTTGTGGCGCATCGCCAACGGTGAAGTA

TTCGGCACCGACACCCCTGTAGAACTGAAACTTCTGGAGATCCCTCAGGCT

CTTGGCGGGGCAGAGGGTGTGGCTATGGAACTTCTGGATTCTGCCTTCCCC

CTCCTGCGAAACATCACCATCACCGCGGATGCCAATGAGGCATTCGACGGC

GCTAATGCGGCGTTTTTGGTCGGTGCGAAGCCTCGCGGAAAAGGCGAAGAG

CGCGCAGATTTGCTGGCTAACAACGGCAAGATTTTCGGACCTCAAGGTAAA

GCTATCAATGACAACGCCGCAGATGACATTCGTGTCCTAGTTGTTGGAAAC

CCAGCGAACACCAACGCGTTGATTGCTTCAGCTGCGGCCCCAGATGTTCCA

GCATCCCGCTTCAACGCAATGATGCGCCTTGATCACAACCGTGCGATCTCC

CAGCTGGCCACCAAGCTTGGCCGTGGATCTGCGGAATTTAACAACATTGTG

GTCTGGGGAAATCACTCCGCAACCCAGTTCCCAGACATCACCTACGCAACC

GTTGGTGGAGAAAAGGTCACTGACCTGGTTGATCACGATTGGTATGTGGAG

GAGTTCATTCCTCGCGTGGCTAACCGTGGCGCTGAAATCATTGAGGTCCGT

GGAAAGTCTTCTGCAGCTTCTGCAGCATCCTCTGCGATTGATCACATGCGC

GATTGGGTACAGGGCACCGAGGCGTGGTCCTCTGCGGCAATTCCTTCCACC

GGTGCATACGGCATTCCTGAGGGCATTTTTGTCGGTCTGCCAACCGTATCC

CGCAACGGTGAGTGGGAAATCGTTGAAGGCCTGGAGATTTCCGATTTCCAG

CGCGCCCGCATCGACGCGAATGCTCAGGAATTGCAGGCCGAGCGCGAGGCA

GTGCGCGACTTGCTCTAA

In the present invention, the malate dehydrogenase derived from *Mannheimia succiniciproducens* may be represented by the following SEQ ID NO: 42. In the present invention, the efficiency of MDH to convert oxaloacetate to malate was improved by substituting the 11$^{th}$ amino acid from Gly to Gln in the following SEQ ID NO: 42.

SEQ ID NO: 42
MKVAVLGAAGGIGQALALLLKLQLPAGSSLSLYDVAPVTPGVAKDLSHIPT

DVVVEGFAGTDPSEALKGADIVLISAGVARKPGMTRADLFGVNAGIIRSLT

EKVAEQCPKACVGIITNPVNAMVAIAAEVLKKAGVYDKRKLFGITTLDILR

AETFIAELKGLDPTRVTIPVIGGHSGVTILPLLSQVQNVEWSSEEEIIALT

HRIQNAGTEVVEAKAGGGSATLSMAQAAARFALALVKASQGAKVVECAYVE

GDGKYARFFAQPVRLGTEGVEEYLTLGKLSAFEEKALNAMLETLQGDIKSG

EDFING

In the present invention, the gene encoding the ii) malate dehydrogenase derived from *Mannheimia succiniciproducens* may be represented by the following SEQ ID NO: 43.

SEQ ID NO: 43
atgaaagttgcagttctaggtgccgcaggcggcattggtcaagcgttggct ttattattaaagttacaattaccggctggttcatctttatctctgtatgat gtcgcacccgtcaccccgggtgttgctaaagatcttagccatatcccaaca gatgttgtggttgaaggttttgccggtacggatccttcagaagcattaaaa ggggcggatattgtgttaatttctgcgggtgtggcacgtaaaccgggcatg acacgtgcggatttattcggtgttaatgcgggtattattcgtagtctgacc gaaaaagtggcggaacaatgcccgaaagcctgtgtgggtattatccaac ccggttaatgcgatggttgccattgcggccgaagtattgaaaaagcgggt gtttacgacaaacgtaaattattcggcattactaccttagatattcttcga gcggaaacctttatcgccgaattaaaaggcttagatcctactcgggttaca attcctgttatcggcggtcattcgggtgtaaccattcttccgttattgtct caagttcaaaatgttgaatggagcagtgaagaggaaatcattgctttaacg catcgtatccaaaatgcaggtacggaagtggttgaagcaaaagcgggcggc ggttctgcaaccttatctatggcgcaggcggcggcacgttttgcattagca ttagtgaaagcctcgcaaggtgcgaaagttgttgaatgcgcttatgtggaa ggcgacggcaaatatgcccgtttctttgcacaaccggttcgtttaggtaca gaaggtgttgaagaatacttaaccctgggtaaattaagtgcatttgaagaa aaagcgttaaatgctatgttagaaactttacaaggtgacattaagtcaggt gaagattttattaacggttaa In the present invention, the malate dehydrogenase wherein the 11$^{th}$ amino acid of the malate dehydrogenase derived from *Mannheimia succiniciproducens* represented by the amino acid sequence of SEQ ID NO: 42 is substituted with glutamine may be represented by the amino acid sequence of the following SEQ ID NO: 44.

SEQ ID NO: 44
MKVAVLGAAGQIGQALALLLKLQLPAGSSLSLYDVAPVTPGVAKDLSHIPT

DVVVEGFAGTDPSEALKGADIVLISAGVARKPGMTRADLFGVNAGIIRSLT

EKVAEQCPKACVGIITNPVNAMVAIAAEVLKKAGVYDKRKLFGITTLDILR

AETFIAELKGLDPTRVTIPVIGGHSGVTILPLLSQVQNVEWSSEEEIIALT

HRIQNAGTEVVEAKAGGGSATLSMAQAAARFALALVKASQGAKVVECAYVE

GDGKYARFFAQPVRLGTEGVEEYLTLGKLSAFEEKALNAMLETLQGDIKSG

EDFING

In the present invention, the gene encoding the malate dehydrogenase derived from *Mannheimia succiniciproducens* represented by the amino acid sequence of SEQ ID NO: 44 may be represented by the amino acid sequence of the following SEQ ID NO: 45.

SEQ ID NO: 45
atgaaagttgcagttctaggtgccgcaggccagattggtcaagcgttggct ttattattaaagttacaattaccggctggttcatctttatctctgtatgat gtcgcacccgtcaccccgggtgttgctaaagatcttagccatatcccaaca gatgttgtggttgaaggttttgccggtacggatccttcagaagcattaaaa ggggcggatattgtgttaatttctgcgggtgtggcacgtaaaccgggcatg acacgtgcggatttattcggtgttaatgcgggtattattcgtagtctgacc gaaaaagtggcggaacaatgcccgaaagcctgtgtgggtattatccaac ccggttaatgcgatggttgccattgcggccgaagtattgaaaaagcgggt gtttacgacaaacgtaaattattcggcattactaccttagatattcttcga gcggaaacctttatcgccgaattaaaaggcttagatcctactcgggttaca attcctgttatcggcggtcattcgggtgtaaccattcttccgttattgtct caagttcaaaatgttgaatggagcagtgaagaggaaatcattgctttaacg catcgtatccaaaatgcaggtacggaagtggttgaagcaaaagcgggcggc ttagtgaaagcctcgcaaggtgcgaaagttgttgaatgcgcttatgtggaa ggcgacggcaaatatgcccgtttctttgcacaaccggttcgtttaggtaca -continued gaaggtgttgaagaatacttaaccctgggtaaattaagtgcatttgaagaa aaagcgttaaatgctatgttagaaactttacaaggtgacattaagtcaggt gaagatttattaacggttaa In the present invention, the microorganism having the ability to produce succinic acid may be selected from the group consisting of Mannheimia sp., Actinobacillus sp., Anaerobiospirillum sp., E. coli, and Corynebacterium sp.

Preferably, the microorganism having the ability to produce succinic acid is Mannheimia succiniciproducens PALK (KCTC10973BP). Also, the microorganism having the ability to produce succinic acid is preferably Basfia sp. variant, which is obtained by deleting a gene encoding a lactate dehydrogenase, a gene encoding a phosphotransacetylase and a gene encoding an acetate kinase in the Basfia sp. strain, which is very similar to Mannheimia succiniciproducens.

In order to further improve the productivity of succinic acid, succinic acid was produced at improved productivity under anaerobic conditions by inoculating the constructed PALKcgmdh strain at a high concentration. Cells were inoculated at an initial high concentration of 8.7 gDCW/L, and fed-batch fermentation was carried out in a limited medium using both glucose and glycerol as dual carbon sources. As a result, 134.25 g/L of succinic acid was produced at a yield of 1.32 mol/mol glucose and productivity of 10.32 g/L/h (FIG. 14; Table 1). These results are superior to the productivity of succinic acid exhibited by E. coli and C. glutamicum using a similar method. Litsanov et al. showed that 134 g/L of succinic acid was obtained at a productivity of 2.53 g/L/h using glucose and formate by inoculating a high concentration of 12.5 gDCW/L of cells using modified C. glutamicum. This shows that the M. succiniciproducens PALKcgmdh strain can produce succinic acid at high productivity and at a high concentration in spite of the use of a lower amount of 8.7 gDCW/L of cells. Also, Vemuri et al. showed that, in the case of E. coli, 99.2 g/L of succinic acid was produced at a productivity per cell of 0.12 g/gDCW/h through a fed-batch fermentation process in which anaerobic culture was started when the cells were at a high concentration. This is very low compared to the M. succiniciproducens PALK (pMS3-cgmdh) strain which produces succinic acid at productivity per cell of 1.19 g/gDCW/h (Litsanov et al., Appl. Environ. Microbiol., 78(9):3325-37, 2012; Vemuri et al., J. Ind. Microbiol. Biotechnol., 28:325-332, 2002).

In another aspect, the present invention is directed to a method for producing succinic acid including: (a) culturing the mutant microorganism to produce succinic acid and (b) recovering the produced succinic acid.

In the present invention, the culture may be carried out using i) glucose, ii) sucrose, iii) glycerol, iv) glucose and glycerol, or v) sucrose and glycerol as carbon sources. The culture may be carried out under anaerobic conditions, or the culture may be carried out by concentrating an initial concentration of the mutant microorganism at an $OD_{600}$ of 15 to 25, but the present invention is not limited thereto. A method of concentrating the mutant microorganism at a high initial concentration may include an inoculum method including injecting a high concentration of mutant microorganism upon inoculation (hereinafter referred to as "inoculum method") or a membrane-cell-recycling bioreactor method (hereinafter, referred to as "MCRB method").

In the present invention, the mutant microorganism may be cultured in a medium having a pH of 6.0 to 7.0, but the present invention is not limited thereto.

EXAMPLE

Hereinafter, the present invention will be described in more detail with reference to examples. However, these examples are suggested only for illustration of the present invention and should not be construed as limiting the scope of the present invention.

In particular, in the following examples, only Mannheimia sp. microorganisms, which are succinic acid-producing microorganisms, are exemplified as host cells for substituting or overexpressing the genes according to the present invention. However, it will be apparent to those skilled in the art that a mutant microorganism having succinic acid productivity similar to that of the present invention can be obtained in spite of the use of other types of succinic acid-producing microorganisms.

Example 1

Construction of MsMDH, CgMDH, EcMDH, ScMDHc, ScMDHm, ScMDHp and YlMDH Over-Expression Vectors (pET30a:MsMDH, pET30a:CgMDH, pET30a:EcVMH, pET30a:ScVMHc, pET30a:ScMDHm, pET30a:ScMDHp, pET30a:YlMDH) and Construction of Mutant Enzyme-Overexpression Vectors (pET30a:MsMDH$^{G11Q}$, pET30a:CgMDH$^{Q20G}$, pET30a:MsMDH$^{L101Q}$, pET30a:CgMDH$^{Q117L}$, pET30a:MsMDH$^{A224S}$, pET30a:CgMDH$^{S242A}$)

Overexpression vectors were each constructed in order to overexpress MDHs of succinic acid-producing microorganisms in E. coli and thereby to obtain proteins. PCR was performed using the primers of SEQ ID NOs: 1 and 2, SEQ ID NOs: 3 and 4, SEQ ID NOs: 5 and 6, and SEQ ID NOs: 7 and 8 and using the genomic DNA of M. succiniciproducens, C. glutamicum, E. coli K12 and Y. lipolytica as templates. The resulting PCR products were cut with NdeI and XhoI restriction enzymes and then cloned into the NdeI and XhoI sites of pET30a (Merck Millipore) to construct overexpression vectors pET30a:MsMDH, pET30a:CgMDH, pET30a:EcMDH and pET30a:YlMDH.

SEQ ID NO: 1:
5'-GCGCCATATGAATTCCCCGCAGAACGTCTCCACC

SEQ ID NO: 2:
5'-GCGCCTCGAG GAGCAAGTCGCGCACTGCCTCGCGC

SEQ ID NO: 3:
5'-GCGCCATATGAAAGTTGCAGTTCTAGGTGCCGCA

SEQ ID NO: 4:
5'-GCGCCTCGAG ACCGTTAATAAAATCTTCACCTGAC

SEQ ID NO: 5:
5'-GCGCCATATGAAAGTCGCAGTCCTCGGCGCTGCT

SEQ ID NO: 6:
5'-GCGCCTCGAGCTTATTAACGAACTCTTCGCCCAG

SEQ ID NO: 7:
5'-GCGCCATATGGTTAAAGCTGTCGTTGCCGGAGCC

SEQ ID NO: 8:
5'-GCGCCTCGAGGTTGGCAGGAGGAGGGTTAACAAT

In order to construct vectors overexpressing three MDHs (ScMDHc, ScMDHm, ScMDHp) derived from S. cerevisiae, PCR was performed using the primers corresponding to SEQ ID NOs: 9 and 10, SEQ ID NOs: 11 and 12, and SEQ ID NOs: 13 and 14 and using the genome of *S. cerevisiae* as a template. The resulting PCR products were cut with NdeI and XhoI restriction enzymes and cloned into NdeI and XhoI sites of pET30a to construct the overexpression vectors pET30a:ScMDHc, pET30a:ScMDHm, and pET30a:ScMDHp.

SEQ ID NO: 9:
5'-GCGCCATATGCCTCACTCAGTTACACCATCCATA

SEQ ID NO: 10:
5'-GCGCCTCGAGAGATGATGCAGATCTCGATGCAAC

SEQ ID NO: 11:
5'-GCGCCATATGTTGTCAAGAGTAGCTAAACGTGCG

SEQ ID NO: 12:
5'-GCGCCTCGAGTTTACTAGCAACAAAGTTGACACC

SEQ ID NO: 13:
5'-GCGCCATATGGTCAAAGTCGCAATTCTTGGCGCT

SEQ ID NO: 14:
5'-GCGCCTCGAGTAGCTTGGAAGAGTCTAGGATGAA

In order to prepare vectors (pET30a:MsMDH$^{G11Q}$, pET30a:MsMDH$^{L101Q}$, pET30a:MsMDH$^{A224S}$) capable of overexpressing mutant enzymes of MsMDH, PCR was conducted using the primers of SEQ ID NOs: 15 and 16, SEQ ID NOs: 17 and 18, and SEQ ID NOs: 19 and 20, respectively, and using pET30a:MsMDH as a template. The resulting PCR products were transformed into *E. coli*, allowed to be selectively grown in LB (Luria-Bertani) solid medium containing kanamycin, and selected. Similarly, in order to prepare vectors (pET30a:CgMDH$^{Q20G}$, pET30a:CgMDHQll$^{7L}$, pET30a:CgMDH$^{S242A}$) capable of overexpressing mutant enzymes of CgMDH, PCR was performed using primers of SEQ ID NOs: 21 and 22, SEQ ID NOs: 23 and 24, and SEQ ID NOs: 25 and 26 and using pET30a:CgMDH as a template. The resulting PCR products were transformed into *E. coli*, allowed to be selectively grown in LB (Luria-Bertani) solid medium containing kanamycin, and extracted. Finally, sequencing was performed to confirm successful mutation.

SEQ ID NO: 15:
5'-CTAGGTGCCGCAGGCCAGATTGGTCAAGCGTTG

SEQ ID NO: 16:
5'-CAACGCTTGACCAATCTGGCCTGCGGCACCTAG

SEQ ID NO: 17:
5'-GGTATTATTCGTAGTCAGACCGAAAAAGTGGCG

SEQ ID NO: 18:
5'-CGCCACTTTTTCGGTCTGACTACGAATAATACC

SEQ ID NO: 19:
5'-GCGGGCGGCGGTTCTTCAACCTTATCTATGGCG

SEQ ID NO: 20:
5'-CGCCATAGATAAGGTTGAAGAACCGCCGCCCGC

SEQ ID NO: 21:
5'-ACCGGCGCAGCTGGTGGCATCTCTTATTCACTG

SEQ ID NO: 22:
5'-CAGTGAATAAGAGATGCCACCAGCTGCGCCGGT

SEQ ID NO: 23:
5'-AAGATTTTCGGACCTCTGGGTAAAGCTATCAATG

SEQ ID NO: 24:
5'-CATTGATAGCTTTACCCAGAGGTCCGAAAATCTT

SEQ ID NO: 25:
5'-GTCCGTGGAAAGTCTGCGGCAGCTTCTGCAGCA

SEQ ID NO: 26:
5'-TGCTGCAGAAGCTGCCGCAGACTTTCCACGGAC

Example 2

Expression and Purification of MsMDH, CgMDH, EcMDH, YlMDH and Mutant Enzyme Proteins Thereof (MsMDH$^{G11Q}$, CgMDH$^{Q20G}$, MsMDH$^{L101Q}$, CgMDH$^{Q117L}$, CgMDH$^{S242A}$)

The overexpression vectors (PET30a:MsMDH, pET30a:CgMDH, pET30a:EcMDH, and pET30a:YlMDH) prepared in Example 1 were transformed into *E. coli* BL21 (DE3)-T1R and cultured in LB medium containing 100 µg/mL of kanamycin at 37° C., and when OD$_{600}$ was 0.6, expression was induced through IPTG. After induction of expression, the cells were further cultured at 18° C. for 20 hours so as to express the corresponding enzyme proteins. The resulting culture solution was centrifuged at 5,000 g for 15 minutes at 4° C. and the cells were then harvested and were lysed by sonication in a buffer A (40 mM Tris-HCl, pH 8.0) kept cold on ice. The cell debris was removed from the obtained cell lysate through centrifugation at 11,000 g for 1 hour. The final supernatant was applied to Ni-NTA agarose beads and MDH proteins with histidine tags were selectively purified via affinity chromatography. After washing the remaining non-specific binding proteins with buffer A containing imidazole at a low concentration of 20 mM, the target proteins were eluted with buffer A containing 300 mM imidazole. For further purification to obtain high-purity proteins, it was possible to obtain MDH proteins with high purity of 95% or more through ion exchange chromatography using HiTrap Q and size exclusion chromatography. The purified MDH proteins were diluted to the concentration of 3 nM, as described in Example 3, and used for activity measurement. The CgMDH and MsMDH proteins were finally concentrated to 54 mg/mL and 42 mg/mL, respectively, and subjected to crystallization.

Example 3

Measurement of Oxaloacetate Reduction Activity of MsMDH, CgMDH, EcMDH, YlMDH, MsMDH$^{G11Q}$, CgMDH$^{Q20G}$, MsMDH$^{L101Q}$, CgMDH$^{Q117L}$, and CgMDH$^{S242A}$ The NADH is used as a cofactor for the oxaloacetate reduction activity of MDH. As a result, NAD+ is produced. The activity of MDH can be measured on an hourly basis through a spectrophotometric method based on the unique absorbance properties of NADH at 340 nm. The composition of the final reaction solution for comparative activity measurement was as follows: 0.1 M Tris-HCl (pH 8.0), 100 µM NADH, 100 µM oxaloacetate, and finally 3 nM purified MDHs (MsMDH, CgMDH, EcMDH, YlMDH). The composition of the final reaction solution for measuring the activity of the mutant enzymes (MsMDH$^{G11Q}$, CgMDH$^{Q20G}$, MsMDH$^{L101Q}$, CgMDH$^{Q117L}$, CgMDH$^{S242A}$) was the same as the composition for measuring the comparative activity. The kinetic activity was measured using final reaction solution while varying the concentration of oxaloacetate and the concentration of NADH under the conditions described above, the concentration of NADH was set at 200 μM when measuring the kinetic activity of oxaloacetate, and the concentration of oxaloacetate was set at 100 μM when measuring the kinetic activity of NADH. Upon graph plotting, the concentration of oxaloacetate (μM) converted per minute was expressed as an initial rate by calculating the decrease in the amount of NADH during the initial reaction time after the addition of the enzyme, as an extinction coefficient. For comparison of the activity depending on pH, the composition (0.1 M buffer, 200 μM NADH, 100 μM oxaloacetate, 3 nM MDH) of the final reaction solution was used. A BIS-tris buffer, a Tris-HCl buffer and a glycine buffer were used at a pH of 5.0 to 6.0, a pH of 7.0 to 9.0, and a pH of 10.0, respectively.

Example 4

Crystallization and Structural Analysis of CgMDH and MsMDH

Initial crystallization of the purified protein was conducted at 20° C. using a screening kit (Hampton Research, CA, USA) through sitting-drop vapor-diffusion. Each experiment was conducted by equilibrating a mixture of 1.0 μL of CgMDH or MsMDH protein and 1.0 μL of a reservoir solution with regard to 0.5 mL of a reservoir solution. CgMDH crystals were found under several crystallization screening conditions and after several cycles of optimization through hanging-drop vapor-diffusion, the crystals having the best quality were found under conditions of 18% PEG 3350, 0.2 M MgCl$_2$ hexahydrate, and 0.1 M HEPES. In order to determine a substrate-binding structure, crystallization was conducted with malate and NAD$^+$ as a substrate to obtain crystals under the same conditions. In the case of MsMDH, high-quality crystals with a size of 0.3×0.3×0.1 mm were obtained in 16% PEG3350 and 8% Tacsimate at pH 6.0 and X-ray diffraction experiments were conducted thereon. In order to determine the substrate-binding structure, crystallization was conducted with NAD$^+$, a substrate, to obtain MsMDH substrate-bound crystals under the same conditions. 30% glycerol contained in the reservoir solution was used to keep the crystals cold conservation, and an X-ray diffraction image of 0.97934 Å wavelength was collected on a 7 Å beamline from the Pohang Accelerator Laboratory via a QUANTUM 270 CCD detector. It was confirmed that CgMDH and NAD$^+$, malate-bound CgMDH crystals, and MsMDH and NAD$^+$-bound MsMDH crystals were diffracted to resolutions of 1.95 Å, 2.00 Å, 2.30 Å and 1.98 Å, respectively. These data were indexed, integrated and scaled using the HKL2000 program. Each of the CgMDH and MsMDH data was phased through the structure of the molecular replacement scheme, *Mycobacterium tuberculosis* MDH (PDB code 4TVO) and *Haemophilus influenzae* MDH (PDB code 6AOO). Model construction was performed using WinCoot and refinement was performed using REFMAC5.

Example 5

Construction of MsMDH, CgMDH, CgMDH$^{Q20G}$ and MsMDH$^{G11Q}$ Overexpression Vectors (pMS3-msmdh, pMS3-cgmdh, pMS3-cgmdh$^{Q20G}$, pMS3-msmdh$^{G11Q}$) and Construction of PALK (pMS3-msmdh), PALK (pMS3-cgmdh), PALK (pMS3-cgmdh$^{Q20G}$) and PALK (pMS3-msmdh$^{G11Q}$) Stains In order to overexpress the MDHs of respective succinic acid-producing microorganisms and determine the effects thereof, as well as to overexpress MDHs modified based on structural analysis and determine the effects thereof, respective overexpression vectors were constructed. First, in order to obtain the MsMDH overexpression vector, pMS3-msmdh, PCR was performed using the primers of SEQ ID NOs: 27 and 28 and the genome of *M. succiniciproducens* as a template. The resulting PCR products were cloned into EcoRI and KpnI sites in pMS3 (Jang et al., Appl. Environ. Microb. 73 (17): 5411-5420, 2007) to complete the pMS3-msmdh vector. In order to obtain the CgMDH overexpression vector, pMS3-cgmdh, PCR was performed using the primers of SEQ ID NOs: 29 and 30 and using the genome of *C. glutamicum* as a template. The resulting PCR product was cloned into the EcoRI and KpnI sites in pMS3 to complete the pMS3-cgmdh vector. PCR was performed using the primers of SEQ ID NOs: 29 and 30 and the CgMDH$^{Q20G}$ gene fragment as a template in order to obtain the CgMDH$^{Q20G}$ overexpression vector, pMS3-cgmdh$^{Q20G}$. The PCR product thus obtained was cloned into EcoRI and KpnI sites in pMS3 to complete the pMS3-cgmdh$^{Q20G}$ vector. PCR was performed using the primers of SEQ ID NOs: 27 and 28 and using the MsMDH$^{G11Q}$ gene fragment as a template in order to obtain the MsMDH$^{G11Q}$ overexpression vector, pMS3-msmdh$^{G11Q}$. The resulting PCR product was cloned into EcoRI and KpnI sites in pMS3 to complete the pMS3-msmdh$^{G11Q}$ vector.

SEQ ID NO: 27:
5'-TATCAACTCTACTGGGGAGGAATTCATGAAAGTTGCAGTTCTAG

SEQ ID NO: 28:
5'-TCTAGAGGATCCCCGGGTACCTTAACCGTTAATAAAATCTTCAC

SEQ ID NO: 29:
5'-TATCAACTCTACTGGGGAGGATGAATTCCCCGCAGAAC

SEQ ID NO: 30:
5'-GGATCCCCGGGTACCGAGCTTTAGAGCAAGTCGCGCAC

Finally, PALK (pMS3-msmdh), PALK (pMS3-cgmdh), PALK (pMS3-cgmdh$^{Q20G}$) and PALK (pMS3-msmdh$^{G11Q}$) strains were each constructed by introducing pMS3-msmdh, pMS3-cgmdh, pMS3-cgmdh$^{Q20G}$ and pMS3-msmdh$^{G11Q}$, produced as described above, into *M. succiniciproducens* PALK (KCTC10973BP). In order to introduce the overexpression vectors described above, *M. succiniciproducens* PALK (KCTC10973BP) was plated on BHI (Brain-Heart Infusion) solid medium and cultured for 36 hours at 39° C., and then colonies were inoculated into 10 mL of BHI liquid medium and cultured for 12 hours. 1 mL of the fully grown cell culture solution was again inoculated in 100 mL of BHI liquid medium and then cultured in a 39° C. incubator. After about 4 to 5 hours, when the cell growth reached about 0.3 to 0.5 of OD$_{600}$, the bacterial cell culture solution was kept at 0 to 4° C. for 20 minutes to prevent the cell growth from further progressing and was then centrifuged at 4° C. and 4,500 rpm for 15 minutes to obtain cells. Then, the cells were resuspended in 200 mL of a 4° C., 10% glycerol solution and then centrifuged again under the same conditions as above. Resuspension and centrifugation were performed in this way a total of three times while halving the amount of 10% glycerol solution that was used. The resulting cells were resuspended in the same volume of 10% glycerol solution, aliquoted, and stored at −80° C. The obtained concentrated cell suspension and four types of overexpressed vectors prepared in this Example were mixed, and electroporation was conducted under the conditions of 2.5 kV, 25 μF and 200Ω to induce the transformation of *M. succiniciproducens* PALK (KCTC10973BP) with the vector.

The cells thus electroporated were recovery-cultured in a BHI liquid medium in a 39° C. incubator for 1 hour, and the culture solution was plated on a BHI solid medium containing 2.5 µg/mL of antibiotic ampicillin, and was cultured in a 39° C. incubator for 48 hours or longer. The mutant strain formed in the medium was cultured in a BHI liquid medium containing an antibiotic and the vector obtained using a vector mini-prep was electrophoresed to confirm the introduction of the overexpression vector.

Example 6

Construction of EcMDH, ZrMDH, ScMDH2 and ScMDH3 Overexpression Vectors (pMS3-ecmdh, pMS3-zrmdh, pMS3-scmdh2, pMS3-scmdh3) and Construction of PALK (pMS3-ecmdh), PALK (pMS3-zrmdh), PALK (pMS3-scmdh2) and PALK (pMS3-scmdh3) Strains.

Respective overexpression vectors were constructed in order to overexpress the MDHs reported in the prior art and to identify the effects thereof. First, PCR was performed using the primers of SEQ ID NOs: 46 and 47 and the genome of E. coli as a template in order to obtain the EcMDH overexpression vector, pMS3-ecmdh. The resulting PCR product was cloned into the EcoRI and KpnI sites in pMS3 to construct the pMS3-ecmdh vector. PCR was performed using the synthesized Zrmdh gene fragment as a template and primers of SEQ ID NOs: 48 and 49 in order to obtain the ZrMDH overexpression vector, pMS3-zrmdh. The resulting PCR product was cloned into the EcoRI and KpnI sites in pMS3 to construct the pMS3-zrmdh vector. PCR was performed using the primers of SEQ ID NOs: 50 and 51 and using the synthesized ScMDH2 gene fragment as a template in order to obtain the ScMDH2 overexpression vector, pMS3-scmdh2. The resulting PCR product was cloned into the EcoRI and KpnI sites in the pMS3 to complete the pMS3-scmdh2 vector. PCR was performed using the primers of SEQ ID NOs: 52 and 53 and using the synthesized ScMDH3 gene fragment as a template in order to obtain the ScMDH3 overexpression vector, pMS3-scmdh3. The resulting PCR product was cloned into the EcoRI and KpnI sites in pMS3 to complete the pMS3-scmdh3 vector.

SEQ ID NO: 46:
5'-TATCAACTCTACTGGGGAGGATGAAAGTCGCAGTCCTC

SEQ ID NO: 47:
5'-TCTAGAGGATCCCCGGGTACTTACTTATTAACGAACTCTTCGC

SEQ ID NO: 48:
5'-TATCAACTCTACTGGGGAGGATGAAAGTTGCAATAGTCG

SEQ ID NO: 49:
5'-TCTAGAGGATCCCCGGGTACCTACAATTTAGCACCGAG

SEQ ID NO: 50:
5'-TATCAACTCTACTGGGGAGGATGCCTCACTCAGTTACAC

SEQ ID NO: 51:
5'-TCTAGAGGATCCCCGGGTACTTAAGATGATGCAGATCTCG

SEQ ID NO: 52:
5'-TATCAACTCTACTGGGGAGGATGGTCAAAGTCGCAATTC

SEQ ID NO: 53:
5'-TCTAGAGGATCCCCGGGTACTCATAGCTTGGAAGAGTC

Finally, PALK (pMS3-ecmdh), PALK (pMS3-zrmdh), PALK (pMS3-scmdh2) and PALK (pMS3-scmdh3) strains were each constructed by introducing pMS3-ecmdh, pMS3-zrmdh, pMS3-scmdh2 and pMS3-scmdh3, produced as described above, into M. succiniciproducens PALK (KCTC10973BP). In order to introduce the overexpression vectors described above, in a manner similar to that of Example 5, M. succiniciproducens PALK (KCTC10973BP) was plated on a BHI solid medium and cultured at 39° C. for 36 hours, and then colonies were inoculated into 10 mL of a BHI liquid medium and cultured for 12 hours. 1 mL of the fully grown cell culture solution was again inoculated in 100 mL of a BHI liquid medium and then cultured in a 39° C. incubator. After about 4 to 5 hours, when the cell growth reached about 0.3 to 0.5 of $OD_{600}$, the bacterial cell culture solution was kept at 0 to 4° C. for 20 minutes to prevent the cell growth from further progressing and was then centrifuged at 4° C. and 4,500 rpm for 15 minutes to obtain cells. Then, the cells were resuspended in 200 mL of a 4° C., 10% glycerol solution and then centrifuged again under the same conditions as above. Resuspension and centrifugation were performed in this way a total of three times while halving the amount of 10% glycerol solution that was used. The resulting cells were resuspended in the same volume of 10% glycerol solution, aliquoted, and stored at −80° C. The obtained concentrated cell suspension and four types of overexpressed vectors prepared in this Example were mixed, and electroporation was conducted under the conditions of 2.5 kV, 25 µF and 200Ω to induce the transformation of M. succiniciproducens PALK (KCTC10973BP) with the vector. The cells thus electroporated were recovery-cultured in a BHI liquid medium in a 39° C. incubator for 1 hour, and the culture solution was plated on a BHI solid medium containing 2.5 µg/mL of antibiotic ampicillin, and was cultured in a 39° C. incubator for 48 hours or longer. The mutant strain formed in the medium was cultured in a BHI liquid medium containing an antibiotic, and the vector obtained using a vector mini-prep was electrophoresed to confirm the introduction of the overexpression vector.

Example 7

Construction of CgMDH Overexpression Vectors for E. coli and C. glutamicum (p100pro99A-cgmdh, pEKEx1-cgmdh) and Construction of E. coli W3110 (p100pro99A-cgmdh) and C. glutamicum (pEKEx1-cgmdh) Strains In order to investigate the overexpression effects of CgMDH in E. coli and C. glutamicum, representative succinic acid-producing strains, CgMDH overexpression vectors for each strain were constructed. First, PCR was performed using the primers of SEQ ID NOs: 54 and 55 using the genome of C. glutamicum as a template in order to obtain the over-expression vector p100pro99A-cgmdh for E. coli. The resulting PCR product was cloned into EcoRI and PstI sites of p100pro99A (Bang et al., Proc Nat. Acad. Sci., 115 (40): E9271-E9279, 2018) to construct the p100pro99A-cgmdh vector. In order to obtain the overexpression vector pEKEx1-cgmdh for C. glutamicum, PCR was performed using the primers of SEQ ID NOs: 56 and 57 and the genome of C. glutamicum as a template. The resulting PCR product was cloned into the EcoRI and PstI sites of pEKEx1 (Cho et al., Metab. Eng. 42: 157-167, 2017) to complete the pEKEx1-cgmdh vector.

SEQ ID NO: 54:
5'-TCCTAGGTACAGTGCTAGCGATGAATTCCCCGCAGAAC

SEQ ID NO: 55:
5'-GCCAAGCTTGCATGCCTGCATTAGAGCAAGTCGCGCAC

-continued

SEQ ID NO: 56:
5'-CAATTTCACACAGGAAACAGATGAATTCCCCGCAGAAC

SEQ ID NO: 57:
5'-AACAGCCAAGCTTGGCTGCATTAGAGCAAGTCGCGCAC

Finally, *E. coli* W3110 (p100pro99A-cgmdh) and *C. glutamicum* (pEKEx1-cgmdh) strains were each developed by introducing p100pro99A-cgmdh and pEKEx1-cgmdh vectors, constructed as described above, into *E. coli* W3110 and wild-type *C. glutamicum*. In order to introduce the overexpression vectors described above, *E. coli* W3110 was plated on LB solid medium and cultured at 37° C. for 24 hours, and then colonies were inoculated into 10 mL of LB liquid medium and cultured for 12 hours. 1 mL of the fully grown cell culture solution was again inoculated in 100 mL of LB liquid medium and then cultured in a 37° C. incubator. After about 4 to 5 hours, when the cell growth reached about 0.3 to 0.5 of $OD_{600}$, the bacterial cell culture solution was kept at 0 to 4° C. for 20 minutes to prevent the cell growth from further progressing and was then centrifuged at 4° C. and 4,500 rpm for 15 minutes to obtain cells. Then, the cells were resuspended in 200 mL of a 4° C., 10% glycerol solution and then centrifuged again under the same conditions as above. Resuspension and centrifugation were performed in this way a total of three times while halving the amount of 10% glycerol solution that was used. The resulting cells were resuspended in the same volume of 10% glycerol solution, aliquoted and stored at −80° C. The obtained concentrated cell suspension and the overexpressed vector p100pro99A-cgmdh prepared in this Example were mixed, and electroporation was conducted under conditions of 1.8 kV, 25 μF and 200Ω to induce the transformation of *E. coli* W3110 with the vector. The cells thus electroporated were recovery-cultured in a LB liquid medium in a 37° C. incubator for 1 hour, and the culture solution was plated on a LB solid medium containing 25 μg/mL of antibiotic ampicillin, and was cultured in a 37° C. incubator for 24 hours or longer. The mutant strain formed in the medium was cultured in a LB liquid medium containing an antibiotic, and the vector obtained using a vector mini-prep was electrophoresed to confirm the introduction of the overexpression vector. In a similar manner as above, *C. glutamicum* was plated on a BHIS (37 g BHI, D-sorbitol 91 g per liter) solid medium and cultured at 30° C. for 24 hours, and then colonies were inoculated into 10 mL of BHIS liquid medium and cultured for 18 hours. 1 mL of the fully grown cell culture solution was again inoculated in 100 mL of a BHIS liquid medium and then cultured in a 30° C. incubator. After about 4 to 5 hours, when the cell growth reached about 0.3 to 0.5 of $OD_{600}$, a concentrated cell suspension was prepared in the same manner as in the case of *E. coli* W3110, and was stored at −80° C. The obtained concentrated cell suspension and the overexpression vector pEKEx1-cgmdh prepared in this Example were mixed, and electroporation was conducted under conditions of 1.8 kV, 25 μF and 200Ω to induce the transformation of *C. glutamicum* with the vector. The cells thus electroporated were recovery-cultured in a BHIS liquid medium in a 30° C. incubator for 2 hours, and the culture solution was plated on a BHIS solid medium containing 25 μg/mL of antibiotic kanamycin, and was cultured in a 30° C. incubator for 24 hours or longer. The mutant strain formed in the medium was cultured in a BHIS liquid medium containing an antibiotic, and the vector obtained using a vector mini-prep was electrophoresed to confirm the introduction of the overexpression vector.

Example 8

Construction of CgMDH and MsMDH$^{G11Q}$ Substitution Vectors (pINcgMDH, pINmsMDH$^{G11Q}$) and Construction of PALKcgmdh and PALKmsmdh$^{G11Q}$ Strains In order to investigate the effects of MDHs naturally occurring in succinic acid-producing strains on the improvement of succinic acid production of PALK (pMS3-cgmdh) and PALK (pMS3-msmdh) strains, genes encoding MDHs present on the genome of *M. succiniciproducens* PALK (KCTC10973BP) strain were deleted, and CgMDH and MsMDH$^{G11Q}$ substitution vectors pINcgMDH and pINmsMDH$^{G11Q}$, inserting genes encoding CgMDH and MsMDH$^{G11Q}$ into the deletion sites, were constructed. For the construction of pINcgMDH, pSacHR06 containing the sacB gene was cut with XhoI and SacI. Then, PCR was performed using primers of SEQ ID NOs: 31 and 32 and SEQ ID NOs: 38 and 39, respectively, with the genome of the *M. succiniciproducens* PALK (KCTC10973BP) strain as a template to obtain front and back sequences of MDH-encoding genes present in the genome. PCR was performed using the primers of SEQ ID NOs: 36 and 37, with the vector containing the chloramphenicol resistance gene as a template to obtain lox66-cat-lox77 cassette. PCR was performed using the primers of SEQ ID NOs: 33 and 35, with the pMS3-cgmdh vector prepared in Example 5 as a template to obtain CgMDH genes. The obtained linear pSacHR06, 1 kb of each of the front and back sequences of MDH-encoding genes, lox66-cat-lox77 cassette and CgMDH gene fragment were combined through Gibson assembly (Gibson et al., Nat. Methods, 6 (5): 343, 2009) to obtain pINcgMDH. The MsMDH$^{G11Q}$ gene fragment required for pINmsMDH$^{G11Q}$ was obtained by performing PCR using the primers of SEQ ID NOs: 33 and 34 with pMS3-msmdh$^{G11Q}$ as a template. The obtained linear pSacHR06, 1 kb of each of the front and back sequences of MDH-encoding gene, lox66-cat-lox77 cassette and MsMDH$^{G11Q}$ gene fragment were combined through Gibson assembly to obtain pINmsMDH$^{G11Q}$. The pINcgMDH and pINmsMDH$^{G11Q}$ thus obtained were introduced into the *M. succiniciproducens* PALK (KCTC10973BP), to finally construct PALKcgmdh and PALKmsmdh$^{G11Q}$ strains, respectively.

SEQ ID NO: 31:
5'-TTCAACGGGAAACGTCTTGCTCGAGCCTTATGTGGACCGAGAAGA

SEQ ID NO: 32:
5'-GGCATTAGCCAACAGAATAGCTGACCGAAAAAGTGGCGGA

SEQ ID NO: 33:
5'-CTATTCTGTTGGCTAATGCC

SEQ ID NO: 34:
5'-TGTAGCCGCGTTCTAACGACTACGAATAATACCCGCAT

SEQ ID NO: 35:
5'-TGTAGCCGCGTTCTAACGTCGACTCTAGAGGATCCCCG

SEQ ID NO: 36:
5'-CGTTAGAACGCGGCTACA

SEQ ID NO: 37:
5'-ATAGGGAGACCGGCAGATC

-continued

SEQ ID NO: 38:
5'-GATCTGCCGGTCTCCCTATTTAAGACTCCTTAATGTGGA

SEQ ID NO: 39:
5'-GCCGCCACCGCGGTGGAGCTCGCGTTAGTTGTTGAGTTAAT

That is, in a manner similar to that of Example 5, *M. succiniciproducens* PALK (KCTC10973BP) was plated on a BHI solid medium and cultured at 39° C. for 3 hours, and then colonies were inoculated into 10 mL of a BHI liquid medium and cultured for 1 hour. 1 mL of the fully grown cell culture solution was again inoculated in 100 mL of a BHI liquid medium and then cultured in a 39° C. incubator. After 4 to 5 hours, when the cell growth reached about 0.3 to 0.5 of $OD_{600}$, the bacterial cell culture solution was kept at 0 to 4° C. for 2 minutes to prevent the cell growth from further progressing and was then centrifuged at 4° C. and 4,500 rpm for 15 minutes to obtain cells. Then, the cells were resuspended in 200 mL of a 4° C., 10% glycerol solution and then centrifuged again under the same conditions as above. Resuspension and centrifugation were performed in this way a total of three times while halving the amount of 10% glycerol solution that was used. The resulting cells were resuspended in the same volume of 10% glycerol solution, aliquoted and stored at −80° C.

The obtained concentrated cell suspension and gene deletion vector pINcgMDH or pINmsMDH$^{G11Q}$ prepared in this Example were mixed, and electroporation was conducted under conditions of 2.5 kV, 25 µF and 200Ω to induce the transformation of *M. succiniciproducens* PALK (KCTC10973BP) with the vectors. The cells thus electroporated were recovery-cultured in a BHI liquid medium in a 39° C. incubator for 1 hour, and the culture solution was plated on a BHI solid medium containing 6.8 µg/mL of chloramphenicol and was cultured in a 39° C. incubator for 48 hours or longer. The colonies formed were plated on a BHI solid medium containing chloramphenicol (6.8 µg/mL) and sucrose (100 g/L), cultured for 24 hours, and then plated again in the same solid medium in order to screen double-crossover colonies.

The mutant strains formed in the medium were cultured in a BHI liquid medium containing an antibiotic and the genomic DNA of the cultured strains were analyzed. PCR was performed using the genomic DNA of the isolated mutant strain as a template, and the obtained PCR products were subjected to electrophoresis to confirm the introduction of CgMDH or MsMDH$^{G11Q}$ and the deletion of the mdh gene in the genomic DNA.

Example 9

Production of Succinic Acid Using *M. succiniciproducens* PALK (pMS3-msmdh), PALK (pMS3-cgmdh), PALK (pMS3-cgmdh$^{Q20G}$) and PALK (pMS3-msmdh$^{G11Q}$) Strains The *M. succiniciproducens* PALK (pMS3-msmdh), PALK (pMS3-cgmdh), PALK (pMS3-cgmdh$^{Q20G}$) and PALK (pMS3-msmdh$^{G11Q}$) strains prepared in Example 5 were cultured under anaerobic conditions at 39° C. for 8 hours in 20 mL of MH5 medium (per liter, 2.5 g yeast extract, 2.5 g polypeptone, 1 g NaCl, 0.02 g $CaCl_2$).$2H_2O$, 0.2 g $MgCl_2.6H_2O$, and 8.709 g $K_2HPO_4$), inoculated with separately sterilized glucose or glycerol at a concentration of 10 g/L as a carbon source, and then cultured in 270 mL of the same medium. Fermentation was carried out by inoculating the culture solution in a microbial reactor (Bioflo 3000, New Brunswick Scientific Co., NJ, USA) containing 2.5 L of a synthetic medium (per liter, 1 g of NaCl, 2 g of $(NH_4)_2HPO_4$, 0.02 g of $CaCl_2.2H_2O$, 0.2 g of $MgCl_2.6H_2O$, 8.709 g of $K_2HPO_4$, 0.5 g of cysteine, 0.5 g of methionine, 0.5 g of alanine, 0.5 g of asparagine, 0.5 g of aspartic acid, 0.5 g of proline, 0.5 g of serine, 0.005 g of nicotinic acid, 0.005 g of Ca-pantothenate, 0.005 g of pyridoxine.HCl, 0.005 g of thiamine, 0.005 g of ascorbic acid and 0.005 g of biotin) and was conducted by feeding pure carbon dioxide at a rate of 0.2 vvm (volume of carbon dioxide/working volume in the reactor/min) at a temperature of 39° C. and at 200 rpm at an initial glucose concentration of 18.2 g/L (100 mM) or an initial glucose and glycerol concentration of 18.2 g/L (100 mM) and 4.6 g/L (50 mM), respectively. During fermentation, the pH was adjusted to 6.5 using 1.57 M ammonia solution and 6.84 M magnesium hydroxide solution, and 25 µg/mL of kanamycin and 25 µg/mL of ampicillin were added as antibiotics. For the production of a high concentration of succinic acid, when the carbon source was completely consumed, 900 g/L of a glucose or glucose and glycerol solution were semi-continuously added as necessary. The cell concentration in the culture medium was measured using a spectrophotometer and the cell concentration was calculated using the previously measured absorbance of the spectrophotometer and the weight calibration line of dry cells. During the fermentation process, samples were periodically collected from the bioreactor. The collected samples were centrifuged at 13,000 rpm for 10 minutes, and concentrations of various metabolites, succinic acid, glucose and glycerol in the supernatant were then analyzed through liquid chromatography.

As a result, as shown in FIG. 11 and Table 1, when only glucose was used as a carbon source, the PALK (pMS3-msmdh) strain produced 79.07 g/L of succinic acid at a yield of 1.23 mol/mol glucose and productivity of 3.26 g/L/h. The PALK (pMS3-cgmdh) strain produced 87.23 g/L of succinic acid at a yield of 1.29 mol/mol glucose and productivity of 3.6 g/L/h. The PALK (pMS3-cgmdh$^{Q20G}$) strain produced 79.39 g/L of succinic acid at a yield of 1.00 mol/mol glucose and productivity of 3.27 g/L/h. Finally, results of fed-batch fermentation of the PALK (pMS3-msmdh$^{G11Q}$) strain showed that 84.19 g/L of succinic acid was produced at a yield and productivity of 1.08 mol/mol glucose and 3.48 g/L/h, respectively. As a result, the PALK (pMS3-cgmdh) strain showed the best ability to produce succinic acid, and the PALK (pMS3-msmdh$^{G11Q}$) strain, which is a modified protein-overexpressing strain constructed based on protein structure analysis, also had improved succinic acid productivity, compared to the *M. succiniciproducens* PALK (KCTC10973BP) strain.

Example 10

Production of Succinic Acid Using *M. succiniciproducens* PALK (pMS3-ecmdh), PALK (pMS3-zrmdh), PALK (pMS3-scmdh2) and PALK (pMS3-scmdh3) Strains The *M. succiniciproducens* PALK (pMS3-ecmdh), PALK (pMS3-zrmdh), PALK (pMS3-scmdh2) and PALK (pMS3-scmdh3) strains prepared in Example 6 were cultured under anaerobic conditions at 39° C. for 8 hours in 20 mL of MH5 medium, inoculated with separately sterilized glucose, as a carbon source, at a concentration of 10 g/L in the same manner as in Example 9, and then cultured in 270 mL of the same medium. Fermentation was carried out by inoculating the culture solution in a microbial reactor containing 2.5 L of a synthetic medium and was conducted by feeding pure carbon dioxide at a rate of 0.2 vvm at a temperature of 39° C. and at 200 rpm at an initial glucose concentration of 18.2 g/L (100 mM). During fermentation, the pH was adjusted to 6.5 using 1.57 M ammonia solution and 6.84 M magnesium hydroxide solution, and 25 µg/mL of kanamycin and 25 µg/mL of ampicillin were added as antibiotics. For the production of a high concentration of succinic acid, when the carbon source was completely consumed, 900 g/L of a glucose solution was semi-continuously added as necessary. The cell concentration in the culture medium was measured using a spectrophotometer, and the cell concentration was calculated using the previously measured absorbance of the spectrophotometer and the weight calibration line of dry cells. During the fermentation process, samples were periodically collected from the bioreactor. The collected samples were centrifuged at 13,000 rpm for 10 minutes, and concentrations of various metabolites, succinic acid, glucose and glycerol in the supernatant were then analyzed through liquid chromatography.

Figure 12:
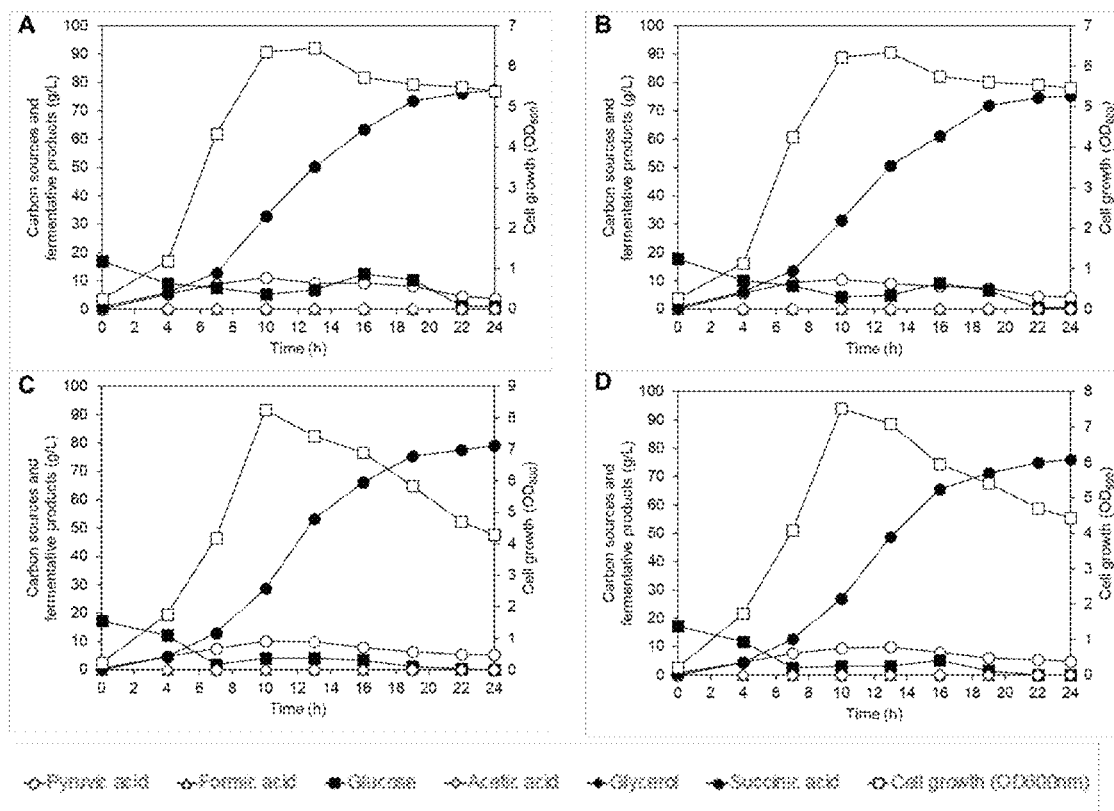
FIG. 12 is a growth and metabolite production curve of *M. succiniciproducens* PALK (pMS3-scmdh2) (A), PALK (pMS3-scmdh3) (B), PALK (pMS3-ecmdh) (C) and PALK (pMS3-zrmdh) (D) strains through fed-batch culture using glucose as a single carbon source.

As a result, as shown in FIG. 12 and Table 1, the PALK (pMS3-msmdh) strain produced 79.05 g/L of succinic acid at a yield of 1.29 mol/mol glucose and productivity of 3.27 g/L/h. The PALK (pMS3-zrmdh) strain produced 76.11 g/L of succinic acid at a yield of 1.25 mol/mol glucose and productivity of 3.15 g/L/h and the PALK (pMS3-scmdh2) strain produced 77.34 g/L of succinic acid at a yield of 1.16 mol/mol glucose and productivity of 3.19 g/L/h. Finally, results of fed-batch fermentation of the PALK (pMS3-scmdh3) strain showed that 75.15 g/L of succinic acid was produced at a yield and productivity of 1.13 mol/mol glucose and 3.1 g/L/h, respectively. These results show that the present invention has improved succinic acid production performance compared to the *M. succiniciproducens* PALK (KCTC10973BP) strain, not overexpressing MDH, as shown in Example 9, but has a lower succinic acid production performance than that of PALK (pMS3-cgmdh) strain. In other words, it demonstrates that CgMDH plays the most important role in the production of succinic acid compared to other MDHs reported in the literature.

Example 11

Production of Succinic Acid Using *E. coli* W3110, *C. glutamicum*, and *E. coli* W3110 (p100pro99A-cgmdh) and *C. glutamicum* (pEKEx1-cgmdh) Strains, Each Overexpressing . . . CgMDH The *E. coli* W3110 (p100pro99A-cgmdh) strain prepared in Example 7 and the *E. coli* W3110 strain were cultured at 37° C. for 16 hours in 10 mL of LB medium inoculated with 3 g/L of separately sterilized glucose as a carbon source and then cultured in 100 mL of the same medium. The initial cell concentration inoculated was adjusted to 0.2 to 0.25 of $OD_{600}$, and the headspace of the flask was filled with carbon dioxide and incubated at 37° C. for 16 hours in an anaerobic condition. 25 µg/mL of ampicillin was added as an antibiotic. As a result, as shown in Table 2, the *E. coli* W3110 (p100pro99A-cgmdh) strain overexpressing CgMDH exhibited remarkably improved production of 0.431 g/L of succinic acid, compared to the conventional *E. coli* W3110 strain producing 0.14 g/L of succinic acid.

The prepared *C. glutamicum* (pEKEx1-cgmdh) and wild-type *C. glutamicum* strains were inoculated in a 10 mL BHIS liquid medium, cultured at 30° C. for 18 hours, and then cultured in 100 mL of the same medium. The initial cell concentration inoculated was adjusted to $OD_{600}$ of 0.2 to 0.25. For cell growth, the cells were cultured in an aerobic environment for the first 6 hours, and then the headspace of the flask was filled with carbon dioxide and the cells were cultured at 30° C. for 10 hours in an anaerobic condition. 25 µg/mL of kanamycin was added as an antibiotic. Isopropyl-β-d-thiogalactopyranoside was added at a final concentration of 0.5 mM to conduct induction. As a result, as shown in Table 2, the *C. glutamicum* (pEKEx1-cgmdh) strain overexpressing CgMDH exhibited significantly higher production of 0.69 g/L of succinic acid than that of the conventional *C. glutamicum* strain showing a production of 0.08 g/L of succinic acid. These results indicate that CgMDH can have a positive effect on the improvement of succinic acid production performance even when it is overexpressed in a common succinic acid-producing strain.

Example 12

Production of Succinic Acid Using *M. succiniciproducens* PALKcgmdh and PALKmsmdh$^{G11Q}$ Strains The *M. succiniciproducens* PALKcgmdh and PALKmsmdh$^{G11Q}$ prepared in Example 8 were cultured under anaerobic conditions at 39° C. for 8 hours in 20 mL of MH5 medium, inoculated with separately sterilized glucose or glucose and glycerol at concentrations of 10 g/L as carbon sources and then cultured in 270 mL of the same medium. Fermentation was carried out by inoculating the culture solution in a microbial reactor containing 2.5 L of a synthetic medium in the same manner as in Example 9 and was conducted by feeding pure carbon dioxide at a rate of 0.2 vvm at a temperature of 39° C. and at 200 rpm at an initial glucose concentration of 18.2 g/L (100 mM) and an initial glycerol concentration of 4.6 g/L (50 mM) in the case of using glucose and glycerol as dual carbon sources. During fermentation, the pH was adjusted to 6.5 using 1.57 M ammonia solution and a 6.84 M magnesium hydroxide solution, and 25 µg/mL of kanamycin and 6.8 µg/mL of chloramphenicol were added as antibiotics. For the production of a high concentration of succinic acid, when the carbon source was completely consumed, 900 g/L of a glucose or glucose and glycerol solutions were semi-continuously added as necessary. The cell concentration in the culture medium was measured using a spectrophotometer, and the cell concentration was calculated using the previously measured absorbance of the spectrophotometer and the weight calibration line of dry cells. During the fermentation process, samples were periodically collected from the bioreactor. The collected samples were centrifuged at 13,000 rpm for 10 minutes, and concentrations of various metabolites, succinic acid, glucose, and glycerol in the supernatant were then analyzed through liquid chromatography.

As a result, as shown in FIG. 13 and Table 1, when only glucose was used as a carbon source, the PALKcgmdh strain produced 89.6 g/L of succinic acid at a yield of 1.28 mol/mol glucose and productivity of 3.71 g/L/h and the PALKmsmdh$^{G11Q}$ strain produced 82.76 g/L of succinic acid at a yield of 1.13 mol/mol glucose and productivity of 3.42 g/L/h.

When both glucose and glycerol were used as dual carbon sources, the PALKcgmdh strain produced 101.18 g/L of succinic acid at a yield of 1.37 mol/mol glucose and productivity of 4.18 g/L/h, and the PALKmsmdh$^{G11Q}$ strain produced 92.5 g/L of succinic acid at a yield of 1.28 mol/mol glucose and productivity of 3.82 g/L/h.

Example 13

Improvement in Productivity of Succinic Acid Using *M. succiniciproducens* PALK (KCTC10973BP) Strain and PALKcgmdh Strain In this Example, a method for improving succinic acid productivity using the *M. succiniciproducens* PALKcgmdh strain was investigated.

As can be seen from FIG. 13 in graph C thereof, the PALKcgmdh strain exhibited maximum productivity 11 to 13 hours after inoculation, and at this time, the cell concentration was maximally increased. Therefore, in order to maximize productivity, first, the change in productivity at a cell concentration higher than the current level was investigated.

Figure 14:
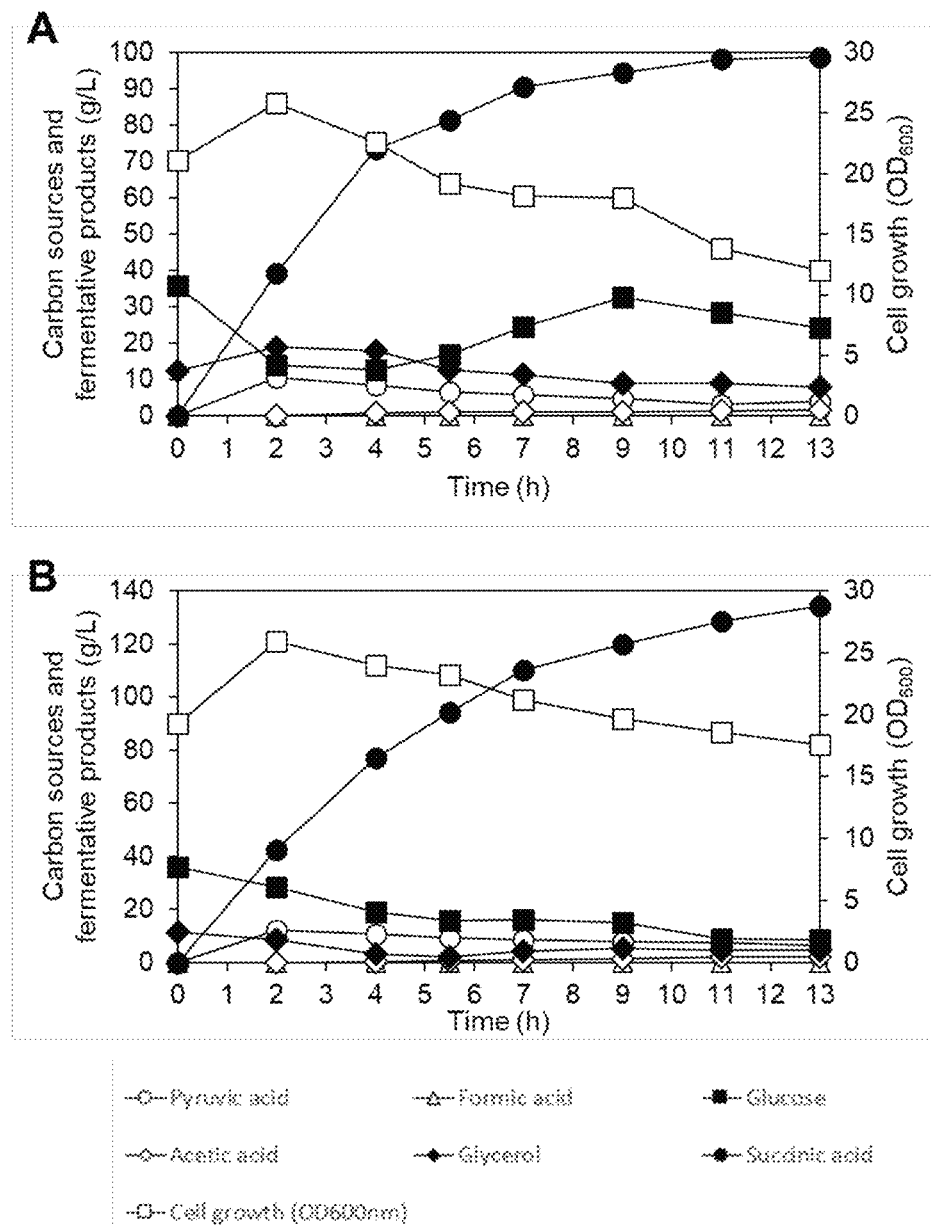
FIG. 14 is a growth and metabolite production curve of fed-batch culture with an increased inoculation amount of *M. succiniciproducens* PALK (KCTC10973BP) strain (A) and PALKcgmdh strain (B).

In order to examine how the productivity of succinic acid changed when the initial cell concentration of the PALKcgmdh strain was increased to $OD_{600}$ of 19.3 (8.7 gDCW/L) the PALKcgmdh strain was inoculated in a microbial reactor containing 2.5 L of a synthetic medium in the same manner as in Example 9. Fermentation upon inoculation was conducted by feeding pure carbon dioxide at a rate of 0.2 vvm at a temperature of 39° C. and at 200 rpm at an initial glucose concentration of 18.2 g/L (100 mM) or an initial glucose and glycerol concentrations of 18.2 g/L (100 mM) and 4.6 g/L (50 mM), respectively, in the case of using glucose and glycerol as dual carbon sources. During fermentation, the pH was adjusted to 6.5 using 1.57 M ammonia solution and a 6.84 M magnesium hydroxide solution, and 25 μg/mL of kanamycin and 6.8 μg/mL of chloramphenicol were added as antibiotics. For the production of a high concentration of succinic acid, when the carbon source was completely consumed, 900 g/L of a glucose and glycerol solution was semi-continuously added as necessary. When PALKcgmdh was cultured for 11 hours to allow the cell concentration to reach the peak, the culture was finished. The resulting culture solution was centrifuged at 4° C. and at 6,000 rpm for 10 minutes to obtain a cell pellet. The cell pellet was resuspended in 200 mL of the same synthetic medium to obtain a high concentration of inoculum. The inoculum was used for inoculation and the cell pellet was cultured under the same conditions as in Example 9, except that the initial glucose and glycerol concentrations were doubled. As a result, succinic acid productivity was 10.32 g/L/h and the maximum productivity was 15.72 g/L/h, which were at least two times higher than in the original fermentation condition, as shown in FIG. 14 and Table 1. In order to re-confirm that the improvement in productivity was due to the effect of strain modification, the succinic acid productivity was observed to be 8.93 g/L/h and the maximum productivity was observed to be 12.4 g/L/h when the initial cell concentration of the *M. succiniciproducens* PALK (KCTC10973BP) strain was also increased to $OD_{600}$ of 21.1 (9.52 gDCW/L). This indicates that the fermentation method of inoculation with a high concentration of cells dramatically increased productivity, but the *M. succiniciproducens* PALKcgmdh strain showed better succinic acid productivity and yield.

TABLE 1

| Strain | Culture condition (carbon sources) | Final SA (g/L) | Final lactic, acetic, formic and pyruvic acids (byproducts in total) (g/L) | Byproducts/SA |
|---|---|---|---|---|
| *M. succiniciproducens* LPK7 (pMS3-zwf-mdh); +zwf from *M. succiniciproducens*, +mdh from *A. thaliana* | CDM (Glu) | 70.09 | 4.23 | 0.06 |
| *Saccharomyces cerevisiae* RWB064; +pckA from *A. succinogenes*, +fumR from *R. oryzae*, +mdh3 from *S. cerevisiae*, +mae1 from *S. pombe* | Batch, 30° C., pH 3, aerobic (OUR = 5 mmol/L/h, 10% CO2), glucose | 16.00 | N/A | N/A |
| *Saccharomyces cerevisiae* CEN.PK113-7D; +gsh1, +cys3, +glr1, +mdh2 from *S. cerevisiae*, +pckA from *M. succinciproducens*, +frdm1 from *T. brucei*, +fumR from *R. oryzae*, +mae1 from *S. pombe* | Fed-batch, 30° C., dual phase (1. aerobic, pH 5, KOH, OUR = 30 mmol/h, 10% CO2; 2. anaerobic, pH release, 10% CO$_2$, 90% N$_2$), glucose | 19.50 | N/A | N/A |
| *Saccharomyces cerevisiae* CEN.PK113-7D; Δadh1, Δadh2, Δgpd1, +pckA from *M. succinciproducens*, +gsh1, +cys3, +glr1, mdh3, and +pyc2p from *S. cerevisiae*, +fumR from *R. oryzae*, +frdm1 from *T. brucei*, +mae1 from *S. pombe* | Fed-batch, 30° C., aerobic, dual phase (1. pH 5; NH$_3$, pO$_2$ = 20%; 2. pH 3; KOH, 50% CO$_2$), glucose | 43.00 | N/A | N/A |
| *Pichia kudriavzevii* CD1822; Δcyb2a, +pyc1 and +fum1 from *C. krusei*, +frd1 from *S. cerevisiae*, +mdh from *Z. rouxii*, +frd1 from *T. brucei* | Batch, 30° C., pH 3, aerobic (DO < 5%, OUR = 10 mmol/L/h, 10% CO$_2$), glucose, KOH | 23.00 | N/A | N/A |
| Evolved strain from the *P. kudriavzevii* ATCC PTA-6658 (high glucose consumption and growth rates); Δura, Δpdc, +pyc1 and +fum from *C. krusei*, +mae from *S. pombe*, +frd from *L. mexicana*, +mdh from *R. delemar* | Batch, 30° C., pH 3, aerobic (DO < 10%, OUR = 18 mmol/L/h, 10% CO$_2$), glucose, KOH | 48.20 | N/A | N/A |

TABLE 1-continued

| Strain | | Overall productivity (g/L/h) | Yield (mol/mol) | Reference |
|---|---|---|---|---|
| E. coli NZN111/pTrc99a-mdh | Dual-phase fermentation | 31.90 | N/A | N/A |
| E. coli NZN111/pTrc99a-mdh | Dual-phase fermentation | 4.30 | N/A | N/A |
| M. succiniciproducens PALKG; +glpK22 Δpta, ackA, ΔldhA | Fed-batch fermentation, Sucrose and glycerol | 66.0 | 0, 0.92, 0, 7.2 (8.12) | 0.12 |
| M. succiniciproducens PALFK; Δpta, ΔackA, ΔldhA, ΔfruA | Fed-batch fermentation, Sucrose and glycerol | 69.2 | 0, 1.23, 0, 0 (1.23) | 0.02 |
| M. succiniciproducens PALFK; Δpta, ΔackA, ΔldhA, ΔfruA | Fed-batch fermentation, Sucrose and glycerol (Initial $OD_{600}$ = 9.0) | 78.4 | 0, 0.72, 0, 1.64 (2.36) | 0.03 |
| M. succiniciproducens PALFK; Δpta, ΔackA, ΔldhA, ΔfruA | Membrane cell recycling bioreactor | 13.2 | 0, 0.65, 0, 3.49 (4.14) | 0.31 |
| PALK (pMS3) | CDM, glucose | 74.56 | 0, 1.37, 0, 6.66 (8.03) | 0.11 |
| PALK (pMS3-msmdh) | CDM, glucose | 79.07 | 0, 0.84, 0, 6.34 (7.18) | 0.09 |
| PALK (pMS3-msmdh$^{G11Q}$) | CDM, glucose | 84.19 | 0, 0.68, 0, 4.42 (5.1) | 0.06 |
| PALK (pMS3-cgmdh) | CDM, glucose | 87.23 | 0, 2.36, 0, 6.12 (8.49) | 0.1 |
| PALK (pMS3-cgmdh$^{Q20G}$) | CDM, glucose | 79.39 | 0, 1.72, 0, 5.78 (7.5) | 0.09 |
| PALK (pMS3-scmdh2) | CDM, glucose | 77.34 | 0, 0, 0, 3.88 (3.88) | 0.05 |
| PALK (pMS3-scmdh3) | CDM, glucose | 75.15 | 0, 0, 0, 4.32 (4.32) | 0.06 |
| PALK (pMS3-ecmdh) | CDM, glucose | 79.05 | 0, 0, 0, 5.15 (5.15) | 0.07 |
| PALK (pMS3-zymdh) | CDM, glucose | 76.11 | 0, 0, 0, 4.79 (4.79) | 0.06 |
| PALKmsmdh$^{G11Q}$ | CDM, glucose | 82.76 | 0, 1.5, 0, 3.56 (5.06) | 0.06 |
| PALKcgmdh | CDM, glucose | 89.6 | 0, 1.3, 0, 6.41 (7.71) | 0.09 |
| PALK | CDM, glucose and glycerol | 90.68 | 0, 2.29, 0, 3.98 (6.27) | 0.07 |
| PALK | CDM, glucose and glycerol, (Initial $OD_{600}$ = 21.1) | 98.28 | 0, 1.42, 0, 3.17 (4.59) | 0.05 |
| PALK (pMS3-cgmdh) | CDM, glucose and glycerol | 101.96 | 0, 1.09, 0, 4.96 (6.05) | 0.06 |
| PALKmsmdh$^{G11Q}$ | CDM, glucose and glycerol | 92.5 | 0, 1.98, 0, 4.92 (6.90) | 0.07 |
| PALKcgmdh | CDM, glucose and glycerol | 101.18 | 0, 1.46, 0, 4.71 (6.17) | 0.06 |
| PALKcgmdh | CDM, glucose and glycerol, (Initial $OD_{600}$ = 19.3) | 134.25 | 0, 6.55, 0, 2.01 (8.56) | 0.06 |

| Strain | Overall productivity (g/L/h) | Yield (mol/mol) | Reference |
|---|---|---|---|
| M. succiniciproducens LPK7 (pMS3-zwf-mdh); +zwf from M. succiniciproducens, +mdh from A. thaliana | 2.6 | 1.51 | Kim et al., Biotechnology journal, 12(2), 1600701. |
| Saccharomyces cerevisiae RWB064; +pckA from A. succinogenes, +fumR from R. oryzae, +mdh3 from S. cerevisiae, +mae1 from S. pombe | 0.18 | N/A | US20110229945A1 |
| Saccharomyces cerevisiae CEN.PK113-7D; +gsh1, +cys3, +glr1, +mdh2 from S. cerevisiae, +pckA from M. succiniciproducens, +frdm1 from T. brucei, +fumR from R. oryzae, +mae1 from S. pombe | 0.22 | N/A | US20120040422A1 |
| Saccharomyces cerevisiae CEN.PK113-7D; Δadh1, Δadh2, Δgpd1, +pckA from M. succiniciproducens, +gsh1, +cys3, +glr1, mdh3, and +pyc2p from S. cerevisiae, +fumR from R. oryzae, +frdm1 from T. brucei, +mae1 from S. pombe | 0.45 | N/A | US20150057425A1 |
| Pichia kudriavzevii CD1822; Δcyb2a, +pyc1 and +fum1 from C. krusei, +frd1 from S. cerevisiae, +mdh from Z. rouxii, +frd1 from T. brucei | 0.26 | N/A | US20130302866A1 |
| Evolved strain from the P. kudriavzevii ATCC PTA-6658 (high glucose consumption and growth rates); Δura, Δpdc, +pyc1 and +fum from C. krusei, +mae from S. pombe, +frd from L. mexicana, +mdh from R. delemar | 0.97 | 0.69 | US20140363862A1 |

TABLE 1-continued

| Strain | Value | Ratio | Reference |
|---|---|---|---|
| E. coli NZN111/pTrc99a-mdh | N/A | 1.19 | Wang et al., Bioprocess Biosyst Eng 2009, 32: 737-745. |
| E. coli NZN111/pTrc99a-mdh | 1.01 | 0.72 | Liang et al., Biotechnology letters, 33(12), 2439-2444. |
| M. succiniciproducens PALKG;+glpK22 Δpta, ΔackA, ΔldhA | 3.34 (max productivity = 6.93) | 1.42 | 1) Lee et al., Metabolic engineering, 38, 409-417. 2) U.S. Pat. No. 8,691,516 B2 |
| M. succiniciproducens PALFK; Δpta, ΔackA, ΔldhA, ΔfruA | 2.50 (max productivity = 4.93) | 1.56 | 1) Lee et al., Metabolic engineering, 38, 409-417. 2) U.S. Pat. No. 8,691,516 B2 |
| M. succiniciproducens PALFK; Δpta, ΔackA, ΔldhA, ΔfruA | 6.03 (max productivity = 10.69) | 1.64 | 1) Lee et al., Metabolic engineering, 38, 409-417. 2) U.S. Pat. No. 8,691,516 B2 |
| M. succiniciproducens PALFK; Δpta, ΔackA, ΔldhA, ΔfruA | 38.6 | 1.22 | 1) Lee et al., Metabolic engineering, 38, 409-417. 2) U.S. Pat. No. 8,691,516 B2 |
| PALK (pMS3) | 3.03 | 1.11 | Ahn et al., J. Ind. Microbiol. Biot., 45(7): 555-566., 2018 |
| PALK (pMS3-msmdh) | 3.26 | 1.23 | This study |
| PALK (pMS3-msmdh$^{G11Q}$) | 3.48 | 1.08 | This study |
| PALK (pMS3-cgmdh) | 3.6 | 1.29 | This study |
| PALK (pMS3-cgmdh$^{Q20G}$) | 3.27 | 1.00 | This study |
| PALK (pMS3-scmdh2) | 3.19 | 1.16 | This study |
| PALK (pMS3-scmdh3) | 3.1 | 1.13 | This study |
| PALK (pMS3-ecmdh) | 3.27 | 1.29 | This study |
| PALK (pMS3-zymdh) | 3.15 | 1.25 | This study |
| PALKmsmdh$^{G11Q}$ | 3.42 | 1.13 | This study |
| PALKcgmdh | 3.71 | 1.28 | This study |
| PALK | 3.49 | 1.15 | Choi et al., Biotechnol. Bioeng., 113(10): 2168-2177., 2016 |
| PALK | 8.93 (max productivity = 12.4) | 1.08 | This study |
| PALK (pMS3-cgmdh) | 4.06 | 1.34 | This study |
| PALKmsmdh$^{G11Q}$ | 3.82 | 1.28 | This study |
| PALKcgmdh | 4.18 | 1.37 | This study |
| PALKcgmdh | 10.32 (max productivity = 15.72) | 1.32 | This study |

TABLE 2

| Strain | Acetic acid (g/L) | Formic acid (g/L) | Lactic acid (g/L) | Pyruvic acid (g/L) | Succinic acid (g/L) | Ethanol (g/L) |
|---|---|---|---|---|---|---|
| E. coli W3110 | 0.521 ± 0.003 | 0.263 ± 0.010 | 0.300 ± 0.004 | 0.153 ± 0.006 | 0.14 ± 0.006 | 0.290 ± 0.008 |
| E. coli W3110 (p100pro99A-cgmdh) | 0.47 ± 0.026 | 0.200 ± 0.047 | 0.547 ± 0.147 | 0.174 ± 0.014 | 0.431 ± 0.010 | 0.351 ± 0.043 |
| Wild-type C. glutamicum | 0.125 ± 0.089 | 0.865 ± 0.145 | 1.036 ± 0.070 | 0 | 0.084 ± 0.118 | 0 |
| C. glutamicum (pEKEx1-cgmdh) | 0.147 ± 0.001 | 0.117 ± 0.015 | 1.708 ± 0.003 | 0.135 ± 0.003 | 0.69 ± 0.009 | 0 |

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims filed and equivalents thereto.

INDUSTRIAL AVAILABILITY

The succinic acid-producing mutant microorganism according to the present invention is characterized in that it expresses a malate dehydrogenase including, glutamine (Gln), as an amino acid residue that interacts with the pyrophosphate moiety of NADH through the amide functional group of the main chain and thus considerably increases the conversion activity from oxaloacetate to malate, thereby capable of producing a high concentration of succinic acid at the highest productivity reported to date when the microorganism is cultured in a limited medium. In addition, the succinic acid-producing mutant microorganism is capable of producing succinic acid at higher productivity and product concentration through more advanced fermentation technology.

The invention claimed is:

1. A mutant microorganism in which the gene encoding a malate dehydrogenase is introduced into *Mannheimia succiniciproducens* PALK (KCTC10973BP),
wherein the malate dehydrogenase comprises the amino acid sequence of SEQ ID NO: 40 or the amino acid sequence of SEQ ID NO: 44, and a gene encoding malate dehydrogenase present in the genome of *Mannheimia succiniciproducens* PALK (KCTC10973BP) is deleted.

2. A method for producing succinic acid comprising:
(a) culturing the mutant microorganism according to claim 1 to produce succinic acid; and
(b) recovering the produced succinic acid.

3. The method according to claim 2, wherein the culture is carried out using i) glucose, ii) sucrose, iii) glycerol, iv) glucose and glycerol, or v) sucrose and glycerol as a carbon source.

4. The method according to claim 2, wherein the culture is carried out under anaerobic conditions.

* * * * *

SEQUENCE LISTING

```
<160> NUMBER OF SEQ ID NOS: 57

<210> SEQ ID NO 1
<211> LENGTH: 34
<212> TYPE: DNA
<213> ORGANISM: Artificial Sequence
<220> FEATURE:
<223> OTHER INFORMATION: Primer

<400> SEQUENCE: 1
gcgccatatg aattccccgc agaacgtctc cacc                         34

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
gcgcctcgag gagcaagtcg cgcactgcct cgcgc                        35

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
gcgccatatg aaagttgcag ttctaggtgc cgca                         34

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
gcgcctcgag accgttaata aaatcttcac ctgac                        35

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
gcgccatatg aaagtcgcag tcctcggcgc tgct                         34

<210> SEQ ID NO 6
<211> LENGTH: 34
<212> TYPE: DNA
<213> ORGANISM: Artificial Sequence
<220> FEATURE:
```

<223> OTHER INFORMATION: Primer

<400> SEQUENCE: 6
gcgcctcgag cttattaacg aactcttcgc ccag                    34

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
gcgccatatg gttaaagctg tcgttgccgg agcc                    34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
gcgcctcgag gttggcagga ggagggttaa caat                    34

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
gcgccatatg cctcactcag ttacaccatc cata                    34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gcgcctcgag agatgatgca gatctcgatg caac                    34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
gcgccatatg ttgtcaagag tagctaaacg tgcg                    34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gcgcctcgag tttactagca acaaagttga cacc                    34

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
gcgccatatg gtcaaagtcg caattcttgg cgct    34

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
gcgcctcgag tagcttggaa gagtctagga tgaa    34

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
ctaggtgccg caggccagat tggtcaagcg ttg    33

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
caacgcttga ccaatctggc ctgcggcacc tag    33

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
ggtattattc gtagtcagac cgaaaaagtg gcg    33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
cgccactttt tcggtctgac tacgaataat acc    33

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
gcgggcggcg gttcttcaac cttatctatg gcg                                33

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
cgccatagat aaggttgaag aaccgccgcc cgc                                33

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
accggcgcag ctggtggcat ctcttattca ctg                                33

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
cagtgaataa gagatgccac cagctgcgcc ggt                                33

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
aagattttcg gacctctggg taaagctatc aatg                               34

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
cattgatagc tttacccaga ggtccgaaaa tctt                               34

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
gtccgtggaa agtctgcggc agcttctgca gca                                33

<210> SEQ ID NO 26
<211> LENGTH: 33

```
<212> TYPE: DNA
<213> ORGANISM: Artificial Sequence
<220> FEATURE:
<223> OTHER INFORMATION: Primer

<400> SEQUENCE: 26
tgctgcagaa gctgccgcag actttccacg gac                          33

<210> SEQ ID NO 27
<211> LENGTH: 44
<212> TYPE: DNA
<213> ORGANISM: Artificial Sequence
<220> FEATURE:
<223> OTHER INFORMATION: Primer

<400> SEQUENCE: 27
tatcaactct actggggagg aattcatgaa agttgcagtt ctag              44

<210> SEQ ID NO 28
<211> LENGTH: 44
<212> TYPE: DNA
<213> ORGANISM: Artificial Sequence
<220> FEATURE:
<223> OTHER INFORMATION: Primer

<400> SEQUENCE: 28
tctagaggat ccccgggtac cttaaccgtt aataaaatct tcac              44

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
tatcaactct actggggagg atgaattccc cgcagaac                     38

<210> SEQ ID NO 30
<211> LENGTH: 38
<212> TYPE: DNA
<213> ORGANISM: Artificial Sequence
<220> FEATURE:
<223> OTHER INFORMATION: Primer

<400> SEQUENCE: 30
ggatccccgg gtaccgagct ttagagcaag tcgcgcac                     38

<210> SEQ ID NO 31
<211> LENGTH: 45
<212> TYPE: DNA
<213> ORGANISM: Artificial Sequence
<220> FEATURE:
<223> OTHER INFORMATION: Primer

<400> SEQUENCE: 31
ttcaacggga aacgtcttgc tcgagcctta tgtggaccga aaga              45

<210> SEQ ID NO 32
<211> LENGTH: 40
<212> TYPE: DNA
<213> ORGANISM: Artificial Sequence
<220> FEATURE:
<223> OTHER INFORMATION: Primer

<400> SEQUENCE: 32
```

```
ggcattagcc aacagaatag ctgaccgaaa aagtggcgga                    40
```

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33

```
ctattctgtt ggctaatgcc                                         20
```

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34

```
tgtagccgcg ttctaacgac tacgaataat acccgcat                     38
```

<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35

```
tgtagccgcg ttctaacgtc gactctagag gatccccg                     38
```

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36

```
cgttagaacg cggctaca                                           18
```

<210> SEQ ID NO 37
<211> LENGTH: 19
<212> TYPE: DNA
<213> ORGANISM: Artificial Sequence
<220> FEATURE:
<223> OTHER INFORMATION: Primer

<400> SEQUENCE: 37

```
atagggagac cggcagatc                                          19
```

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38

```
gatctgccgg tctccctatt taagactcct taatgtgga                    39
```

<210> SEQ ID NO 39
<211> LENGTH: 41
<212> TYPE: DNA
<213> ORGANISM: Artificial Sequence

```
<220> FEATURE:
<223> OTHER INFORMATION: Primer

<400> SEQUENCE: 39
gccgccaccg cggtggagct cgcgttagtt gttgagttaa t                 41

<210> SEQ ID NO 40
<211> LENGTH: 328
<212> TYPE: PRT
<213> ORGANISM: Artificial Sequence
<220> FEATURE:
<223> OTHER INFORMATION: Synthetic Construct

<400> SEQUENCE: 40
```

| Met | Asn | Ser | Pro | Gln | Asn | Val | Ser | Thr | Lys | Lys | Val | Thr | Val | Thr | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Ala | Gly | Gln | Ile | Ser | Tyr | Ser | Leu | Leu | Trp | Arg | Ile | Ala | Asn | Gly |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Glu | Val | Phe | Gly | Thr | Asp | Thr | Pro | Val | Glu | Leu | Lys | Leu | Leu | Glu | Ile |
|-----|-----|-----|-----|-----|-----|-----|-----|-----|-----|-----|-----|-----|-----|-----|-----|
|     |     |     |     | 35  |     |     |     |     | 40  |     |     |     |     | 45  |     |

| Pro | Gln | Ala | Leu | Gly | Gly | Ala | Glu | Gly | Val | Ala | Met | Glu | Leu | Leu | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Ala | Phe | Pro | Leu | Leu | Arg | Asn | Ile | Thr | Ile | Thr | Ala | Asp | Ala | Asn |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Glu | Ala | Phe | Asp | Gly | Ala | Asn | Ala | Ala | Phe | Leu | Val | Gly | Ala | Lys | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Arg | Gly | Lys | Gly | Glu | Glu | Arg | Ala | Asp | Leu | Leu | Ala | Asn | Asn | Gly | Lys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Phe | Gly | Pro | Gln | Gly | Lys | Ala | Ile | Asn | Asp | Asn | Ala | Ala | Asp | Asp |
|-----|-----|-----|-----|-----|-----|-----|-----|-----|-----|-----|-----|-----|-----|-----|-----|
|     |     |     |     | 115 |     |     |     |     | 120 |     |     |     |     | 125 |     |

| Ile | Arg | Val | Leu | Val | Val | Gly | Asn | Pro | Ala | Asn | Thr | Asn | Ala | Leu | Ile |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Ser | Ala | Ala | Ala | Pro | Asp | Val | Pro | Ala | Ser | Arg | Phe | Asn | Ala | Met |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Met | Arg | Leu | Asp | His | Asn | Arg | Ala | Ile | Ser | Gln | Leu | Ala | Thr | Lys | Leu |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Gly | Arg | Gly | Ser | Ala | Glu | Phe | Asn | Asn | Ile | Val | Val | Trp | Gly | Asn | His |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Ala | Thr | Gln | Phe | Pro | Asp | Ile | Thr | Tyr | Ala | Thr | Val | Gly | Gly | Glu |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Lys | Val | Thr | Asp | Leu | Val | Asp | His | Asp | Trp | Tyr | Val | Glu | Glu | Phe | Ile |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Pro | Arg | Val | Ala | Asn | Arg | Gly | Ala | Glu | Ile | Ile | Glu | Val | Arg | Gly | Lys |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ser | Ser | Ala | Ala | Ser | Ala | Ala | Ser | Ala | Ile | Asp | His | Met | Arg | Asp |
|-----|-----|-----|-----|-----|-----|-----|-----|-----|-----|-----|-----|-----|-----|-----|
|     |     |     |     | 245 |     |     |     |     | 250 |     |     |     |     | 255 |

| Trp | Val | Gln | Gly | Thr | Glu | Ala | Trp | Ser | Ser | Ala | Ala | Ile | Pro | Ser | Thr |
|-----|-----|-----|-----|-----|-----|-----|-----|-----|-----|-----|-----|-----|-----|-----|-----|
|     |     |     |     | 260 |     |     |     |     | 265 |     |     |     |     | 270 |     |

| Gly | Ala | Tyr | Gly | Ile | Pro | Glu | Gly | Ile | Phe | Val | Gly | Leu | Pro | Thr | Val |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Ser | Arg | Asn | Gly | Glu | Trp | Glu | Ile | Val | Glu | Gly | Leu | Glu | Ile | Ser | Asp |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Phe | Gln | Arg | Ala | Arg | Ile | Asp | Ala | Asn | Ala | Gln | Glu | Leu | Gln | Ala | Glu |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Arg | Glu | Ala | Val | Arg | Asp | Leu | Leu |
|-----|-----|-----|-----|-----|-----|-----|-----|
|     |     |     |     | 325 |     |     |     |

<210> SEQ ID NO 41
<211> LENGTH: 987
<212> TYPE: DNA
<213> ORGANISM: Artificial Sequence
<220> FEATURE:
<223> OTHER INFORMATION: Synthetic Construct

<400> SEQUENCE: 41

```
atgaattccc cgcagaacgt ctccaccaag aaggtcaccg tcaccggcgc agctggtcaa      60
atctcttatt cactgttgtg gcgcatcgcc aacggtgaag tattcggcac cgacacccct     120
gtagaactga aacttctgga gatccctcag gctcttggcg gggcagaggg tgtggctatg     180
gaacttctgg attctgcctt ccccctcctg cgaaacatca ccatcaccgc ggatgccaat     240
gaggcattcg acggcgctaa tgcggcgttt ttggtcggtg cgaagcctcg cggaaaaggc     300
gaagagcgcg cagatttgct ggctaacaac ggcaagattt cggacctca aggtaaagct      360
atcaatgaca cgccgcaga tgacattcgt gtcctagttg ttggaaaccc agcgaacacc      420
aacgcgttga ttgcttcagc tgcggcccca gatgttccag catcccgctt caacgcaatg     480
atgcgccttg atcacaaccg tgcgatctcc cagctggcca ccaagcttgg ccgtggatct     540
gcggaattta caacattgt ggtctgggga atcactccg caacccagtt cccagacatc       600
acctacgcaa ccgttggtgg agaaaaggtc actgacctgg ttgatcacga ttggtatgtg     660
gaggagttca ttcctcgcgt ggctaaccgt ggcgctgaaa tcattgaggt ccgtggaaag     720
tcttctgcag cttctgcagc atcctctgcg attgatcaca tgcgcgattg ggtacagggc     780
accgaggcgt ggtcctctgc ggcaattcct tccaccggtg catacggcat tcctgagggc     840
attttttgtcg gtctgccaac cgtatcccgc aacggtgagt gggaaatcgt tgaaggcctg     900
gagatttccg atttccagcg cgcccgcatc gacgcgaatg ctcaggaatt gcaggccgag     960
cgcgaggcag tgcgcgactt gctctaa                                        987
```

<210> SEQ ID NO 42
<211> LENGTH: 312
<212> TYPE: PRT
<213> ORGANISM: Unknown
<220> FEATURE:
<223> OTHER INFORMATION: Mannheimia succiniciproducens

<400> SEQUENCE: 42

Met Lys Val Ala Val Leu Gly Ala Ala Gly Gly Ile Gly Gln Ala Leu
1               5                   10                  15

Ala Leu Leu Leu Lys Leu Gln Leu Pro Ala Gly Ser Ser Leu Ser Leu
            20                  25                  30

Tyr Asp Val Ala Pro Val Thr Pro Gly Val Ala Lys Asp Leu Ser His
        35                  40                  45

Ile Pro Thr Asp Val Val Glu Gly Phe Ala Gly Thr Asp Pro Ser
    50                  55                  60

Glu Ala Leu Lys Gly Ala Asp Ile Val Leu Ile Ser Ala Gly Val Ala
65                  70                  75                  80

Arg Lys Pro Gly Met Thr Arg Ala Asp Leu Phe Gly Val Asn Ala Gly
            85                  90                  95

Ile Ile Arg Ser Leu Thr Glu Lys Val Ala Glu Gln Cys Pro Lys Ala
        100                 105                 110

Cys Val Gly Ile Ile Thr Asn Pro Val Asn Ala Met Val Ala Ile Ala
    115                 120                 125

```
Ala Glu Val Leu Lys Lys Ala Gly Val Tyr Asp Lys Arg Lys Leu Phe
        130                 135                 140
Gly Ile Thr Thr Leu Asp Ile Leu Arg Ala Glu Thr Phe Ile Ala Glu
145                 150                 155                 160
Leu Lys Gly Leu Asp Pro Thr Arg Val Thr Ile Pro Val Ile Gly Gly
                165                 170                 175
His Ser Gly Val Thr Ile Leu Pro Leu Leu Ser Gln Val Gln Asn Val
            180                 185                 190
Glu Trp Ser Ser Glu Glu Ile Ile Ala Leu Thr His Arg Ile Gln
        195                 200                 205
Asn Ala Gly Thr Glu Val Val Glu Ala Lys Ala Gly Gly Ser Ala
    210                 215                 220
Thr Leu Ser Met Ala Gln Ala Ala Arg Phe Ala Leu Ala Leu Val
225                 230                 235                 240
Lys Ala Ser Gln Gly Ala Lys Val Val Glu Cys Ala Tyr Val Glu Gly
                245                 250                 255
Asp Gly Lys Tyr Ala Arg Phe Phe Ala Gln Pro Val Arg Leu Gly Thr
            260                 265                 270
Glu Gly Val Glu Glu Tyr Leu Thr Leu Gly Lys Leu Ser Ala Phe Glu
        275                 280                 285
Glu Lys Ala Leu Asn Ala Met Leu Glu Thr Leu Gln Gly Asp Ile Lys
    290                 295                 300
Ser Gly Glu Asp Phe Ile Asn Gly
305                 310
```

```
<210> SEQ ID NO 43
<211> LENGTH: 939
<212> TYPE: DNA
<213> ORGANISM: Unknown
<220> FEATURE:
<223> OTHER INFORMATION: Mannheimia succiniciproducens

<400> SEQUENCE: 43
atgaaagttg cagttctagg tgccgcaggc ggcattggtc aagcgttggc tttattatta      60
aagttacaat taccggctgg ttcatcttta tctctgtatg atgtcgcacc cgtcaccccg     120
ggtgttgcta agatcttag ccatatccca acagatgttg tggttgaagg ttttgccggt      180
acggatcctt cagaagcatt aaaaggggcg gatattgtgt taatttctgc gggtgtggca     240
cgtaaaccgg gcatgacacg tgcggattta ttcggtgtta atgcgggtat tattcgtagt     300
ctgaccgaaa agtggcgga caatgcccg aaagcctgtg tgggtattat caccaacccg       360
gttaatgcga tggttgccat tgcggccgaa gtattgaaaa aagcgggtgt ttacgacaaa     420 cgtaaaattat tcggcattac taccttagat attcttcgag cggaaacctt tatcgccgaa    480
ttaaaaggct tagatcctac tcgggttaca attcctgtta tcggcggtca ttcgggtgta    540
accattcttc cgttattgtc tcaagttcaa aatgttgaat ggagcagtga agaggaaatc    600
attgctttaa cgcatcgtat ccaaaatgca ggtacggaag tggttgaagc aaaagcgggc    660
ggcggttctg caaccttatc tatggcgcag gcggcggcac gttttgcatt agcattagtg    720
aaagcctcgc aaggtgcgaa agttgttgaa tgcgcttatg tggaaggcga cggcaaatat    780
gcccgtttct ttgcacaacc ggttcgttta ggtacagaag gtgttgaaga atacttaacc    840
ctgggtaaat taagtgcatt tgaagaaaaa gcgttaaatg ctatgttaga aactttacaa    900
ggtgacatta agtcaggtga agatttttatt aacggttaa                          939
```

<210> SEQ ID NO 44
<211> LENGTH: 312
<212> TYPE: PRT
<213> ORGANISM: Artificial Sequence
<220> FEATURE:
<223> OTHER INFORMATION: G11Q from Mannheimia succiniciproducens MDH

<400> SEQUENCE: 44

Met Lys Val Ala Val Leu Gly Ala Ala Gly Gln Ile Gly Gln Ala Leu
1               5                   10                  15

Ala Leu Leu Lys Leu Gln Leu Pro Ala Gly Ser Ser Leu Ser Leu
            20                  25                  30

Tyr Asp Val Ala Pro Val Thr Pro Gly Val Ala Lys Asp Leu Ser His
        35                  40                  45

Ile Pro Thr Asp Val Val Glu Gly Phe Ala Gly Thr Asp Pro Ser
50                  55                  60

Glu Ala Leu Lys Gly Ala Asp Ile Val Leu Ile Ser Ala Gly Val Ala
65                  70                  75                  80

Arg Lys Pro Gly Met Thr Arg Ala Asp Leu Phe Gly Val Asn Ala Gly
                85                  90                  95

Ile Ile Arg Ser Leu Thr Glu Lys Val Ala Glu Gln Cys Pro Lys Ala
            100                 105                 110

Cys Val Gly Ile Ile Thr Asn Pro Val Asn Ala Met Val Ala Ile Ala
        115                 120                 125

Ala Glu Val Leu Lys Lys Ala Gly Val Tyr Asp Lys Arg Lys Leu Phe
    130                 135                 140

Gly Ile Thr Thr Leu Asp Ile Leu Arg Ala Glu Thr Phe Ile Ala Glu
145                 150                 155                 160

Leu Lys Gly Leu Asp Pro Thr Arg Val Thr Ile Pro Val Ile Gly Gly
                165                 170                 175

His Ser Gly Val Thr Ile Leu Pro Leu Leu Ser Gln Val Gln Asn Val
            180                 185                 190

Glu Trp Ser Ser Glu Glu Ile Ile Ala Leu Thr His Arg Ile Gln
        195                 200                 205

Asn Ala Gly Thr Glu Val Val Glu Ala Lys Ala Gly Gly Gly Ser Ala
    210                 215                 220

Thr Leu Ser Met Ala Gln Ala Ala Arg Phe Ala Leu Ala Leu Val
225                 230                 235                 240

Lys Ala Ser Gln Gly Ala Lys Val Val Glu Cys Ala Tyr Val Glu Gly
                245                 250                 255

Asp Gly Lys Tyr Ala Arg Phe Phe Ala Gln Pro Val Arg Leu Gly Thr
            260                 265                 270

Glu Gly Val Glu Glu Tyr Leu Thr Leu Gly Lys Leu Ser Ala Phe Glu
        275                 280                 285

Glu Lys Ala Leu Asn Ala Met Leu Glu Thr Leu Gln Gly Asp Ile Lys
    290                 295                 300

Ser Gly Glu Asp Phe Ile Asn Gly
305                 310

<210> SEQ ID NO 45
<211> LENGTH: 939
<212> TYPE: DNA
<213> ORGANISM: Artificial Sequence
<220> FEATURE:
<223> OTHER INFORMATION: G11Q from Mannheimia succiniciproducens MDH

<400> SEQUENCE: 45

```
atgaaagttg cagttctagg tgccgcaggc cagattggtc aagcgttggc tttattatta      60
aagttacaat taccggctgg ttcatcttta tctctgtatg atgtcgcacc cgtcaccccg     120
ggtgttgcta aagatcttag ccatatccca acagatgttg tggttgaagg ttttgccggt     180
acggatcctt cagaagcatt aaaagggcg gatattgtgt taatttctgc gggtgtggca      240
cgtaaaccgg gcatgacacg tgcggattta ttcggtgtta atgcgggtat tattcgtagt     300
ctgaccgaaa aagtggcgga acaatgcccg aaagcctgtg tgggtattat caccaacccg     360
gttaatgcga tggttgccat tgcggccgaa gtattgaaaa agcgggtgt ttacgacaaa      420
cgtaaattat tcggcattac taccttagat attcttcgag cggaaacctt tatcgccgaa     480
ttaaaaggct tagatcctac tcgggttaca attcctgtta tcggcggtca ttcgggtgta     540
accattcttc cgttattgtc tcaagttcaa aatgttgaat ggagcagtga agaggaaatc     600
attgctttaa cgcatcgtat ccaaaatgca ggtacggaag tggttgaagc aaaagcgggc     660
ggcggttctg caaccttatc tatggcgcag gcggcggcac gttttgcatt agcattagtg     720
aaagcctcgc aaggtgcgaa agttgttgaa tgcgcttatg tggaaggcga cggcaaatat     780
gcccgtttct ttgcacaacc ggttcgttta ggtacagaag gtgttgaaga atacttaacc     840
ctgggtaaat aagtgcatt tgaagaaaaa gcgttaaatg ctatgttaga aactttacaa      900
ggtgacatta agtcaggtga agattttatt aacggttaa                             939
```

```
<210> SEQ ID NO 46
<211> LENGTH: 38
<212> TYPE: DNA
<213> ORGANISM: Artificial Sequence
<220> FEATURE:
<223> OTHER INFORMATION: Primer

<400> SEQUENCE: 46
tatcaactct actggggagg atgaaagtcg cagtcctc                              38

<210> SEQ ID NO 47
<211> LENGTH: 43
<212> TYPE: DNA
<213> ORGANISM: Artificial Sequence
<220> FEATURE:
<223> OTHER INFORMATION: Primer

<400> SEQUENCE: 47
tctagaggat ccccgggtac ttacttatta acgaactctt cgc                        43

<210> SEQ ID NO 48
<211> LENGTH: 39
<212> TYPE: DNA
<213> ORGANISM: Artificial Sequence
<220> FEATURE:
<223> OTHER INFORMATION: Primer

<400> SEQUENCE: 48
tatcaactct actggggagg atgaaagttg caatagtcg                             39

<210> SEQ ID NO 49
<211> LENGTH: 38
<212> TYPE: DNA
<213> ORGANISM: Artificial Sequence
<220> FEATURE:
<223> OTHER INFORMATION: Primer

<400> SEQUENCE: 49
tctagaggat ccccgggtac ctacaattta gcaccgag                              38
```

<210> SEQ ID NO 50
<211> LENGTH: 39
<212> TYPE: DNA
<213> ORGANISM: Artificial Sequence
<220> FEATURE:
<223> OTHER INFORMATION: Primer

<400> SEQUENCE: 50
tatcaactct actggggagg atgcctcact cagttacac                                  39

<210> SEQ ID NO 51
<211> LENGTH: 40
<212> TYPE: DNA
<213> ORGANISM: Artificial Sequence
<220> FEATURE:
<223> OTHER INFORMATION: Primer

<400> SEQUENCE: 51
tctagaggat ccccgggtac ttaagatgat gcagatctcg                                 40

<210> SEQ ID NO 52
<211> LENGTH: 39
<212> TYPE: DNA
<213> ORGANISM: Artificial Sequence
<220> FEATURE:
<223> OTHER INFORMATION: Primer

<400> SEQUENCE: 52
tatcaactct actggggagg atggtcaaag tcgcaattc                                  39

<210> SEQ ID NO 53
<211> LENGTH: 38
<212> TYPE: DNA
<213> ORGANISM: Artificial Sequence
<220> FEATURE:
<223> OTHER INFORMATION: Primer

<400> SEQUENCE: 53
tctagaggat ccccgggtac tcatagcttg gaagagtc                                   38

<210> SEQ ID NO 54
<211> LENGTH: 38
<212> TYPE: DNA
<213> ORGANISM: Artificial Sequence
<220> FEATURE:
<223> OTHER INFORMATION: Primer

<400> SEQUENCE: 54
tcctaggtac agtgctagcg atgaattccc cgcagaac                                   38

<210> SEQ ID NO 55
<211> LENGTH: 38
<212> TYPE: DNA
<213> ORGANISM: Artificial Sequence
<220> FEATURE:
<223> OTHER INFORMATION: Primer

<400> SEQUENCE: 55
gccaagcttg catgcctgca ttagagcaag tcgcgcac                                   38

<210> SEQ ID NO 56
<211> LENGTH: 38
<212> TYPE: DNA
<213> ORGANISM: Artificial Sequence
<220> FEATURE:

```
<223> OTHER INFORMATION: Primer

<400> SEQUENCE: 56
caatttcaca caggaaacag atgaattccc cgcagaac                              38

<210> SEQ ID NO 57
<211> LENGTH: 38
<212> TYPE: DNA
<213> ORGANISM: Artificial Sequence
<220> FEATURE:
<223> OTHER INFORMATION: Primer

<400> SEQUENCE: 57
aacagccaag cttggctgca ttagagcaag tcgcgcac                              38
```

UNITED STATES PATENT AND TRADEMARK OFFICE
CERTIFICATE OF CORRECTION

PATENT NO. : 11,655,462 B2
APPLICATION NO. : 16/490515
DATED : May 23, 2023
INVENTOR(S) : Sang Yup Lee et al.

It is certified that error appears in the above-identified patent and that said Letters Patent is hereby corrected as shown below:

In the Specification

Column 14, Line 26, "pET30a:EcVMH" should be -- pET30a:EcMDH --.

Column 14, Line 27, "pET30a:ScVMHc" should be -- pET30a:ScMDHc --.

Column 15, Line 35, "CgMDHQ117L" should be -- CgMDH$^{Q117L}$ --.

Column 23, Line 61, "CaCl$_2$).2H$_2$O" should be -- CaCl$_2$•2H$_2$O --.

In the Claims

Column 57, Line 26, "a gene" should be -- the gene --.

Signed and Sealed this
Eleventh Day of July, 2023

Katherine Kelly Vidal
*Director of the United States Patent and Trademark Office*